United States Patent
Zhao et al.

(10) Patent No.: US 11,882,990 B2
(45) Date of Patent: *Jan. 30, 2024

(54) SYSTEMS AND METHODS FOR DATA FILTERING OF PASSAGEWAY SENSOR DATA

(71) Applicant: INTUITIVE SURGICAL OPERATIONS, INC., Sunnyvale, CA (US)

(72) Inventors: Tao Zhao, Sunnyvale, CA (US); Timothy D. Soper, San Jose, CA (US)

(73) Assignee: INTUITIVE SURGICAL OPERATIONS, INC, Sunnyvale, CA (US)

( * ) Notice: Subject to any disclaimer, the term of this patent is extended or adjusted under 35 U.S.C. 154(b) by 1217 days.

This patent is subject to a terminal disclaimer.

(21) Appl. No.: 16/481,954

(22) PCT Filed: Feb. 1, 2018

(86) PCT No.: PCT/US2018/016446
§ 371 (c)(1),
(2) Date: Jul. 30, 2019

(87) PCT Pub. No.: WO2018/144726
PCT Pub. Date: Aug. 9, 2018

(65) Prior Publication Data
US 2019/0365199 A1    Dec. 5, 2019

Related U.S. Application Data

(60) Provisional application No. 62/453,341, filed on Feb. 1, 2017.

(51) Int. Cl.
*A61B 34/20*    (2016.01)
*A61B 34/10*    (2016.01)
(Continued)

(52) U.S. Cl.
CPC .............. *A61B 34/20* (2016.02); *A61B 1/005* (2013.01); *A61B 1/00006* (2013.01);
(Continued)

(58) Field of Classification Search
CPC ... A61B 34/20; A61B 1/009; A61B 2034/105; A61B 2034/2061
See application file for complete search history.

(56) References Cited

U.S. PATENT DOCUMENTS 8,494,612 B2    7/2013    Vetter et al.
2012/0029339 A1    2/2012    Cohen et al.
(Continued)

FOREIGN PATENT DOCUMENTS

CN    103079478 A    5/2013
EP    1421913 B1    4/2012
(Continued)

OTHER PUBLICATIONS

International Preliminary Report on Patentability for Application No. PCT/US2018/016446, dated Aug. 15, 2019, 08 pages.
(Continued)

*Primary Examiner* — Jason M Ip
(74) *Attorney, Agent, or Firm* — Haynes & Boone, LLP

(57) ABSTRACT

A system and method for data filtering of passageway sensor data include traversing a plurality of passageways with a flexible elongate device and recording, during the traversing, positional data using one or more sensors coupled to the flexible elongate device. The positional data includes a first plurality of positional data points recorded during a first insertion of the flexible elongate device into a first passageway and a second plurality of positional data points recorded during a first retraction of the flexible elongate device within the first passageway. The system and method further include labeling the first plurality of positional data points and the (Continued)

second plurality of positional data points as first common passageway positional data points and registering the positional data with a model of the plurality of passageways, wherein the registering includes matching the first common passageway positional data points with corresponding first common passageway model data points.

17 Claims, 14 Drawing Sheets

(51) Int. Cl.
*A61B 17/00* (2006.01)
*A61B 1/00* (2006.01)
*A61B 1/005* (2006.01)

(52) U.S. Cl.
CPC ........ *A61B 1/009* (2022.02); *A61B 17/00234* (2013.01); *A61B 34/10* (2016.02); *A61B 2017/00296* (2013.01); *A61B 2034/105* (2016.02); *A61B 2034/2061* (2016.02)

(56) References Cited

U.S. PATENT DOCUMENTS

| | | | |
|---|---|---|---|
| 2012/0203067 A1 | 8/2012 | Higgins et al. | |
| 2012/0289777 A1* | 11/2012 | Chopra | A61B 1/00055 382/128 |
| 2013/0303892 A1 | 11/2013 | Zhao et al. | |
| 2014/0276002 A1* | 9/2014 | West | A61B 5/061 600/424 |
| 2015/0057575 A1* | 2/2015 | Tsusaka | A61B 34/37 600/587 |

FOREIGN PATENT DOCUMENTS

| | | |
|---|---|---|
| EP | 2881037 A1 | 6/2015 |
| WO | WO-2013169814 A1 | 11/2013 |
| WO | WO-2016077419 A1 | 5/2016 |
| WO | WO-2016191298 A1 | 12/2016 |

OTHER PUBLICATIONS

International Search Report and Written Opinion for application No. PCT/US2018/016446, dated May 14, 2018, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

```
deepestQuantizedDepth = round (initialDepth / binSize);   // Process 1102
previousDepth = initialDepth;                              // Process 1102
while (getPosition(depth, position)) {                     // Process 1104
    curBin = round ((depth - initialDepth) / binSize);    // Process 1106
    direction = sign(depth - previousDepth);              // Process 1108
    if (direction == 1 || direction == 0) {               // Process 1108
        Add position to insertBin[curBin];                // Process 1110
        if (curBin > deepestQuantizedDepth )              // Process 1112
            deepestQuantizedDepth = curBin;               // Process 1114
    }
    else {
        Add location to retractBin[curBin];               // Process 1116
        while (deepestBint > curBin) {                    // Process 1118
            a1 = aggregate(insertBin[deepestQuantizedDepth ]);  // Process 1120
            a2 = aggregate(retractBin[deepestQuantizedDepth ]); // Process 1120
            newPosition = aggregate(a1, a2);              // Process 1120
            Output newPosition;                           // Process 1122
            clear (insertBin[deepestQuantizedDepth ];     // Process 1124
            clear (retractBin[deepestQuantizedDepth ];    // Process 1124
            --deepestQuantizedDepth ;                     // Process 1126
    }
}
```

Fig. 11B

| Bin # | Insertion | Retraction |
|---|---|---|
| i | $P_1\ P_2\ P_3$ | |
| i+1 | | |
| i+2 | $P_4\ P_5$ | |
| i+3 | $P_6\ P_7\ P_8\ P_9\ P_{10}$ | |
| i+4 | $P_{11}\ P_{12}\ P_{13}$ | $P_{14}\ P_{15}\ P_{16}$ |

Fig. 12A

← Deepest insertion depth for current cycle

| Bin # | Insertion | Retraction |
|---|---|---|
| i | $P_1\ P_2\ P_3$ | |
| i+1 | | |
| i+2 | $P_4\ P_5$ | |
| i+3 | $P_6\ P_7\ P_8\ P_9\ P_{10}$ | $P_{17}$ |
| i+4 | Aggregate & Clear | Aggregate & Clear |

Fig. 12B

← Deepest insertion depth for current cycle

| Bin # | Insertion | Retraction |
|---|---|---|
| i | $P_1\ P_2\ P_3$ | |
| i+1 | | |
| i+2 | $P_4\ P_5$ | |
| i+3 | $P_6\ P_7\ P_8\ P_9\ P_{10}$ | $P_{17}\ P_{18}\ P_{19}$ |
| i+4 | | |

Fig. 12C

← Deepest insertion depth for current cycle

| Bin # | Insertion | Retraction |
|---|---|---|
| i | $P_1\ P_2\ P_3$ | |
| i+1 | | $P_{20}$ |
| i+2 | Aggregate & Clear | ---------------------- |
| i+3 | Aggregate & Clear | Aggregate & Clear |
| i+4 | | |

← Deepest insertion depth for current cycle

Fig. 12D

SYSTEMS AND METHODS FOR DATA FILTERING OF PASSAGEWAY SENSOR DATA

RELATED APPLICATIONS

This patent application is a U.S. National Stage patent application of International Patent Application No. PCT/US2018/016446 filed on Feb. 1, 2018, the benefit of which is claimed, and claims priority to and benefit of the filing date of U.S. Provisional Patent Application No. 62/453,341, entitled "System and Method for Minimizing Sensor Error and Perturbation of Passageway Data," filed Feb. 1, 2017, each of which is incorporated by reference herein in its entirety.

FIELD

The present disclosure is directed to systems and methods for conducting an image-guided procedure, and more particularly to systems and methods for data filtering of passageway sensor data.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditional instrument tracking and referencing systems may require the use of patient pads during pre-operative and operative imaging and may disturb the clinical environment or workflow. Systems and methods for performing image-guided surgery with minimal clinical disturbances are needed.

SUMMARY

The embodiments of the invention are best summarized by the claims that follow the description.

Consistent with some embodiments, a method includes traversing a plurality of passageways with a flexible elongate device and recording, during the traversing, positional data using one or more sensors coupled to the flexible elongate device. The positional data includes a first plurality of positional data points recorded during a first insertion of the flexible elongate device into a first passageway and a second plurality of positional data points recorded during a first retraction of the flexible elongate device within the first passageway. The method further includes labeling the first plurality of positional data points and the second plurality of positional data points as first common passageway positional data points and registering the positional data with a model of the plurality of passageways, wherein the registering includes matching the first common passageway positional data points with corresponding first common passageway model data points.

Consistent with some embodiments, a method includes inserting a flexible elongate device into a passageway, recording a first positional data from the flexible elongate device at an insertion distance during the insertion, retracting the flexible elongate device, recording a second positional data from the flexible elongate device at the insertion distance during the retraction, and combining the first and second positional data to create a third positional data.

Consistent with some embodiments, a medical system includes an elongated flexible device, a tracking system for determining positional data of the elongated flexible device, an actuator system for providing motion of the elongate flexible device within a plurality of anatomical passageways of a patient, and one or more hardware processors coupled to the tracking system and the actuator system. The motion includes insertion and retraction within the plurality of anatomical passageways. The one or more hardware processors are configured to record the positional data and register the positional data with a model of the plurality of anatomical passageways of the patient. The positional data is comprised of a plurality of positional data points each associated with corresponding motion of the elongated flexible device at a time each of the plurality of positional data points is recorded. The registering is based at least in part on the association between each of the positional data points and the corresponding motion.

Consistent with some embodiments, a non-transitory machine-readable medium includes a plurality of machine-readable instructions which when executed by one or more processors associated with a device are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 5A:
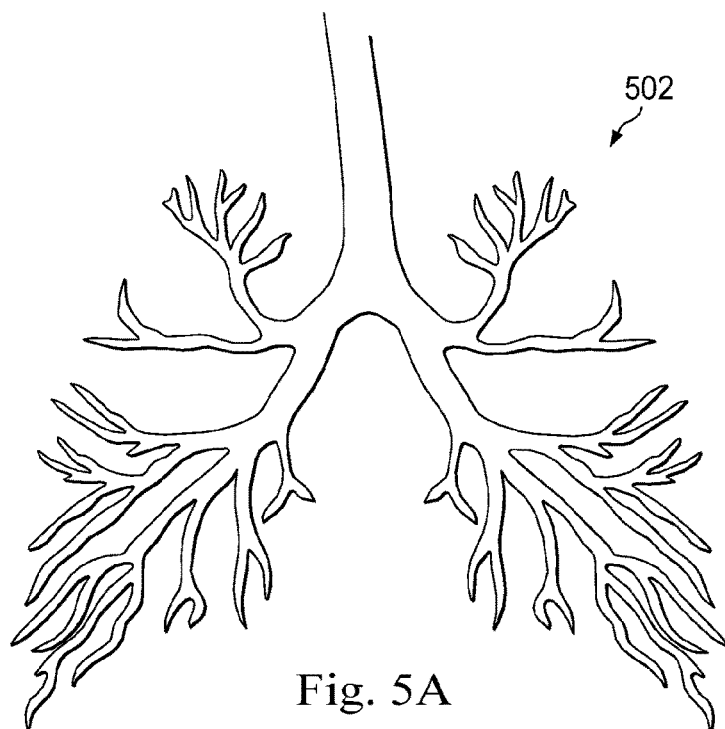
Figure 5B:
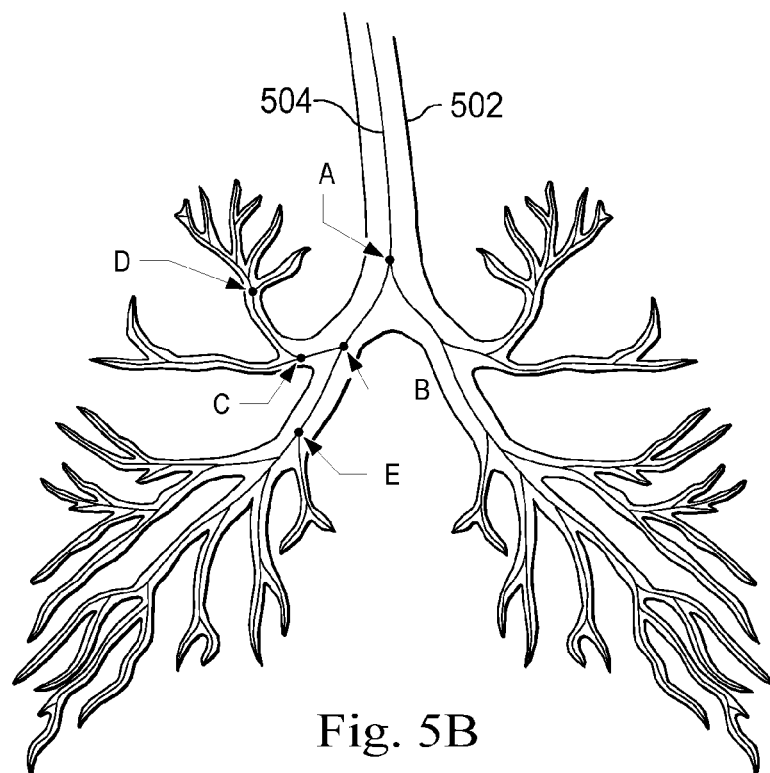
Figure 5C:
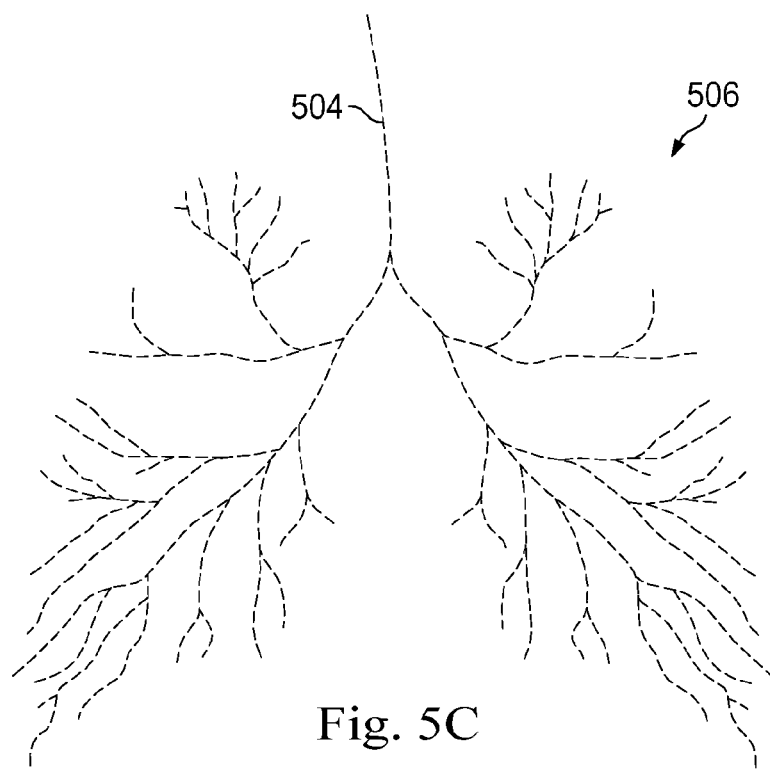

FIGS. 5A, 5B, and 5C illustrate exemplary application of processes in a segmentation method that generates a model of human lungs for registration.

Figure 6A:
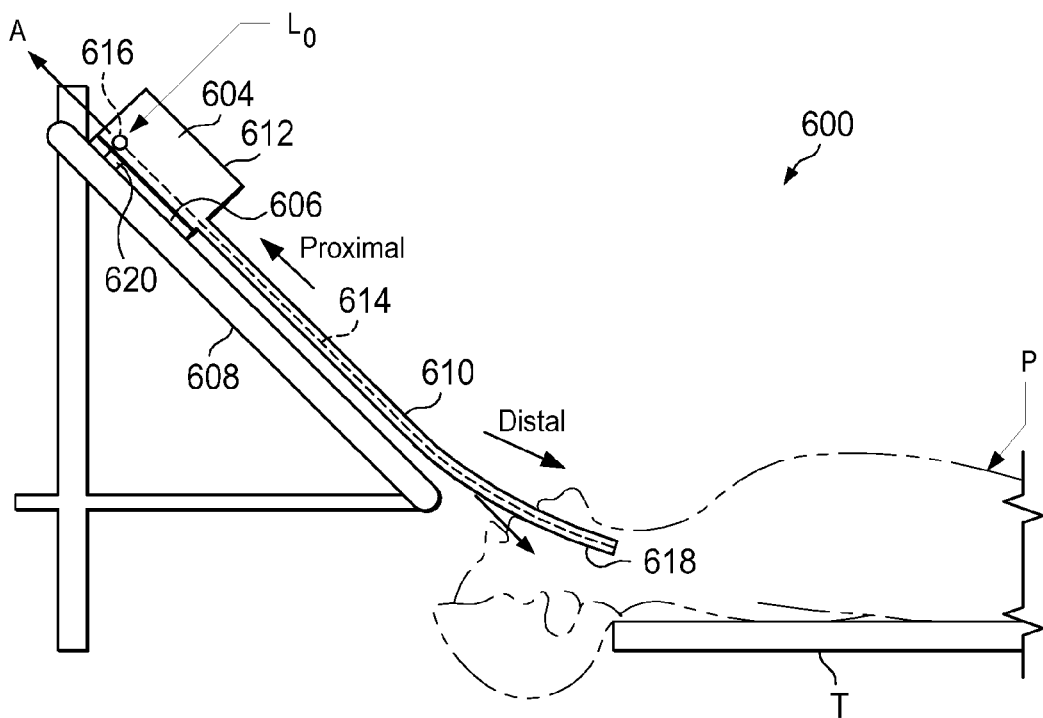
Figure 6B:
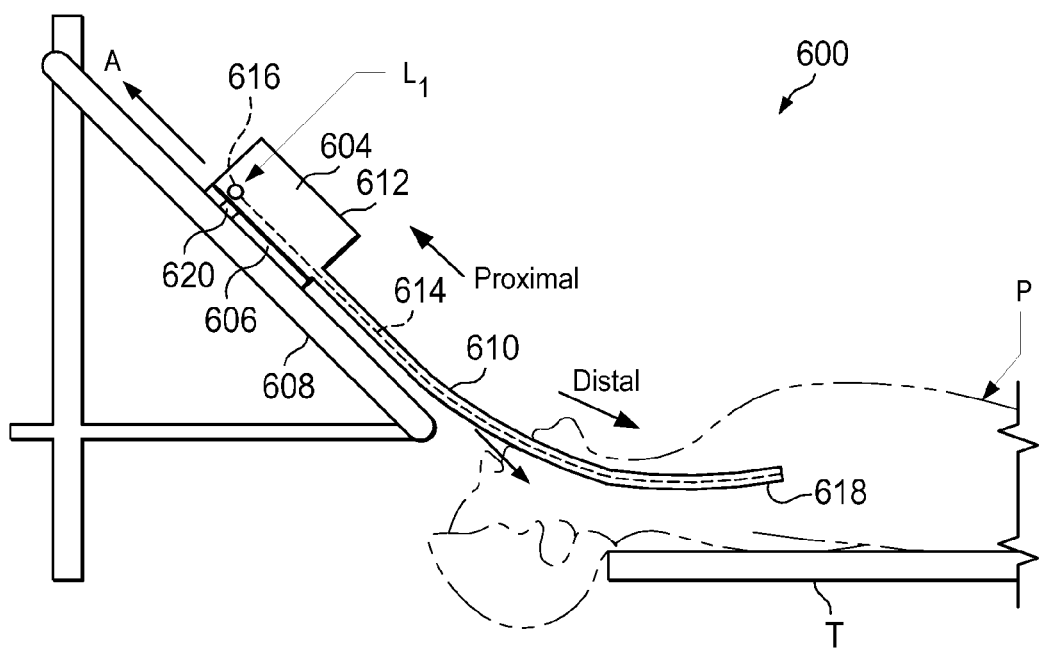

FIGS. 6A and 6B are exemplary side views of a patient coordinate space including a medical instrument mounted on an insertion assembly.

Figure 6C:
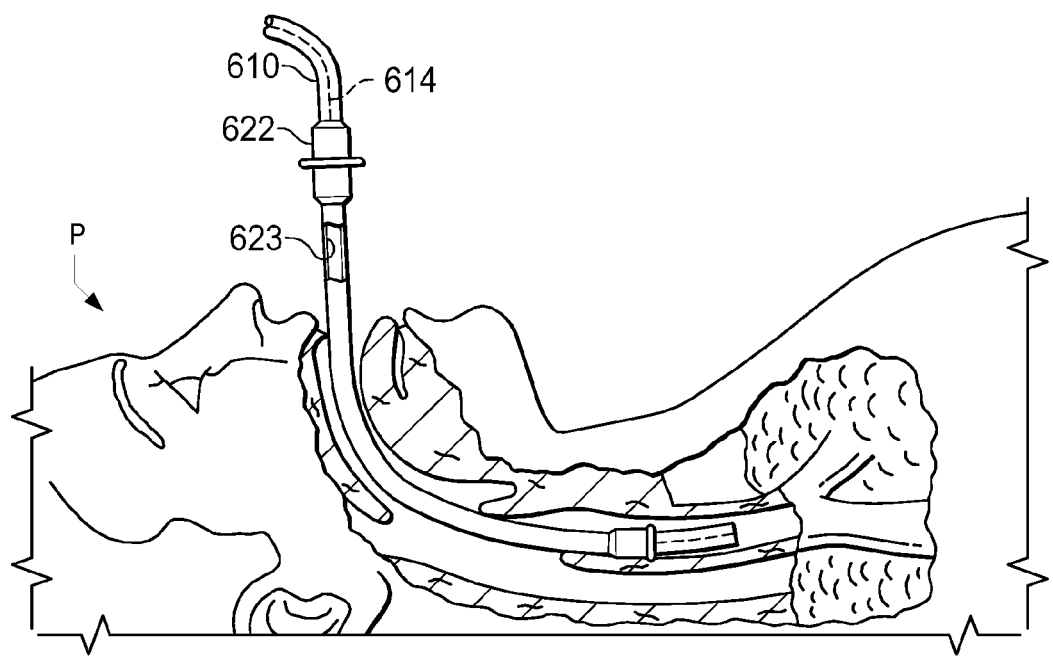

FIG. 6C is an exemplary side view of a patient in a patient coordinate space including an endotracheal tube.

Figure 7:
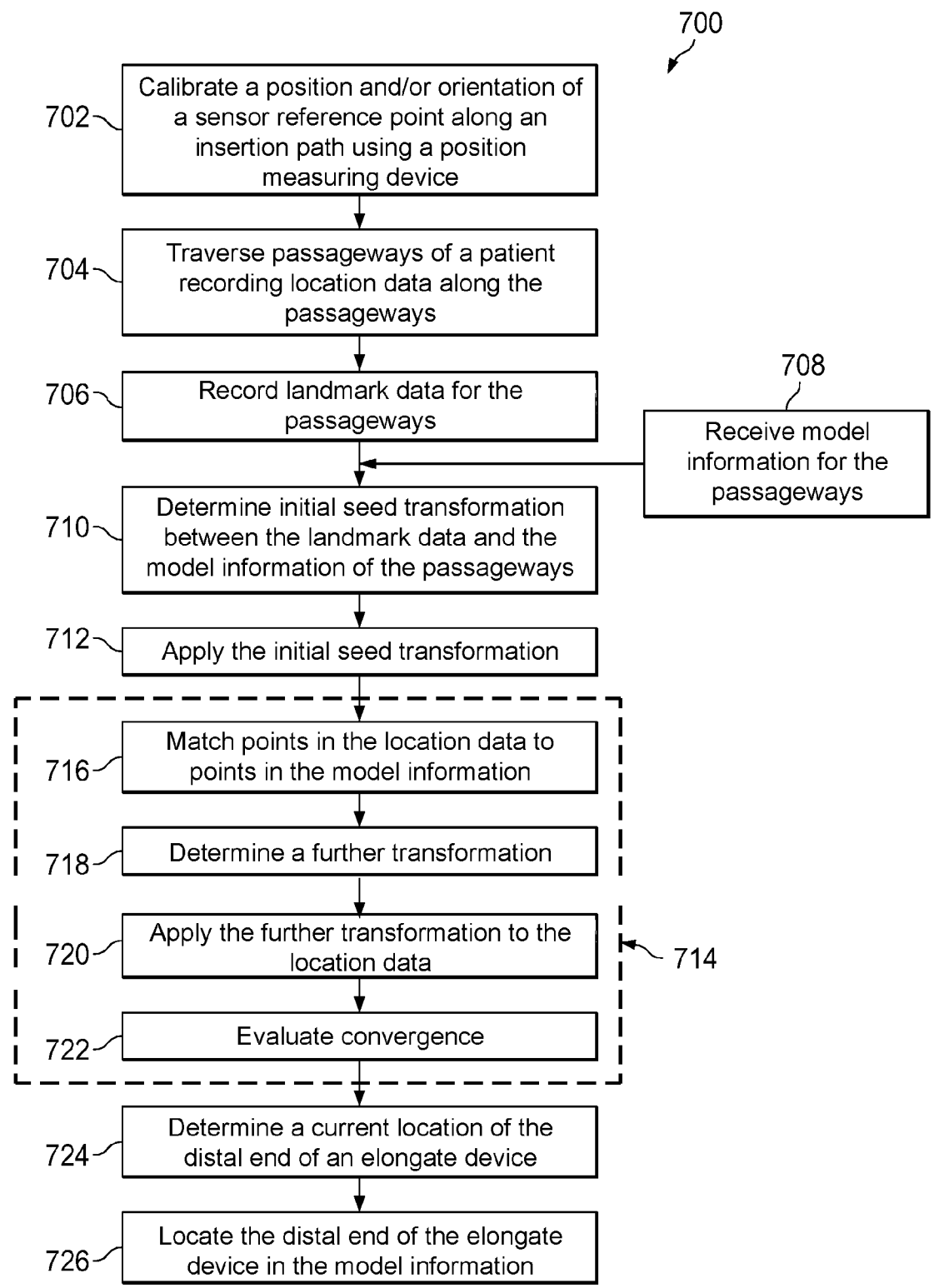

FIG. 7 illustrates a flowchart of an exemplary method of providing guidance for an image-guided surgical procedure.

Figure 8:
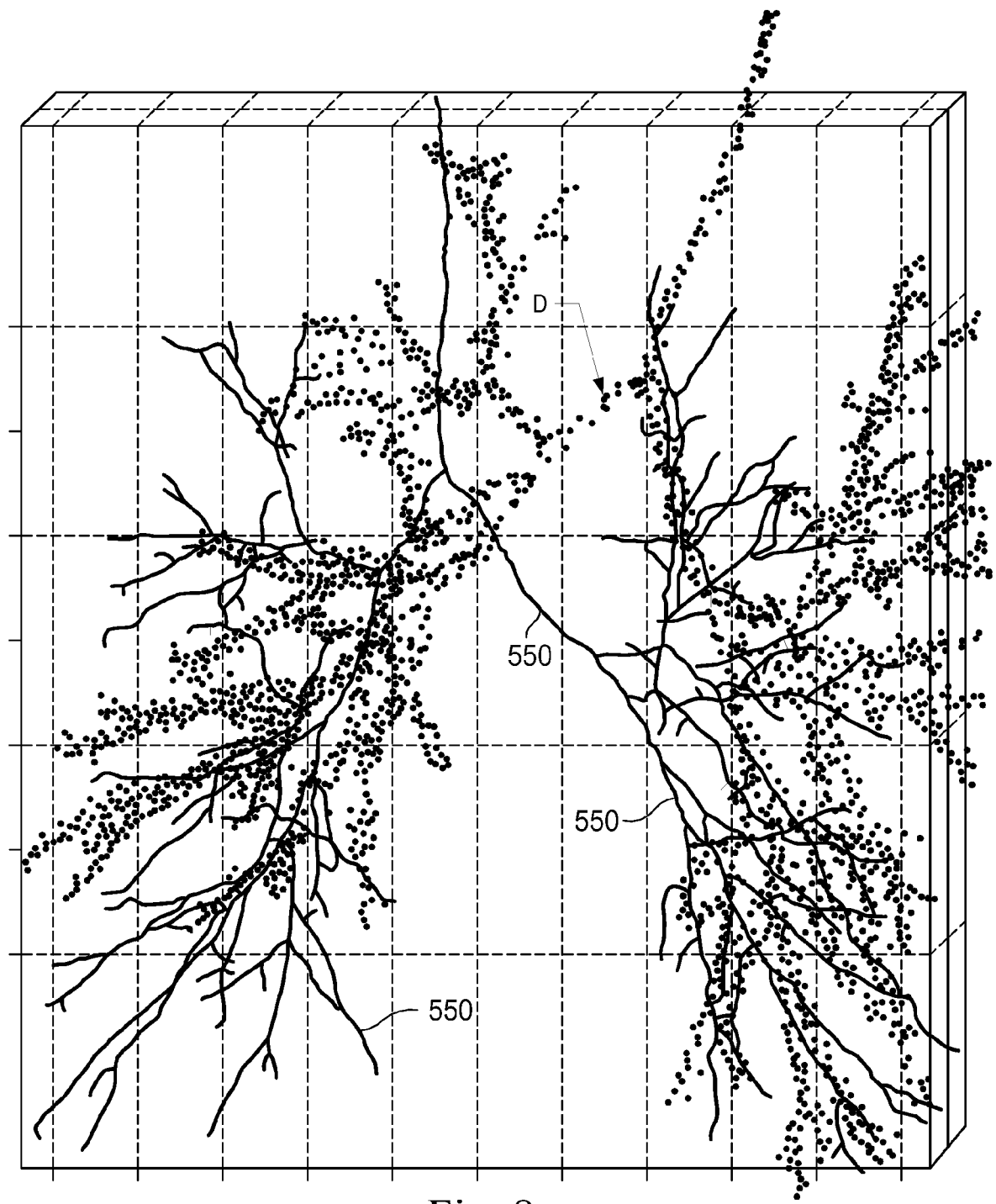

FIG. 8 illustrates exemplary location data collected by traversing airways in human lungs.

Figure 9:
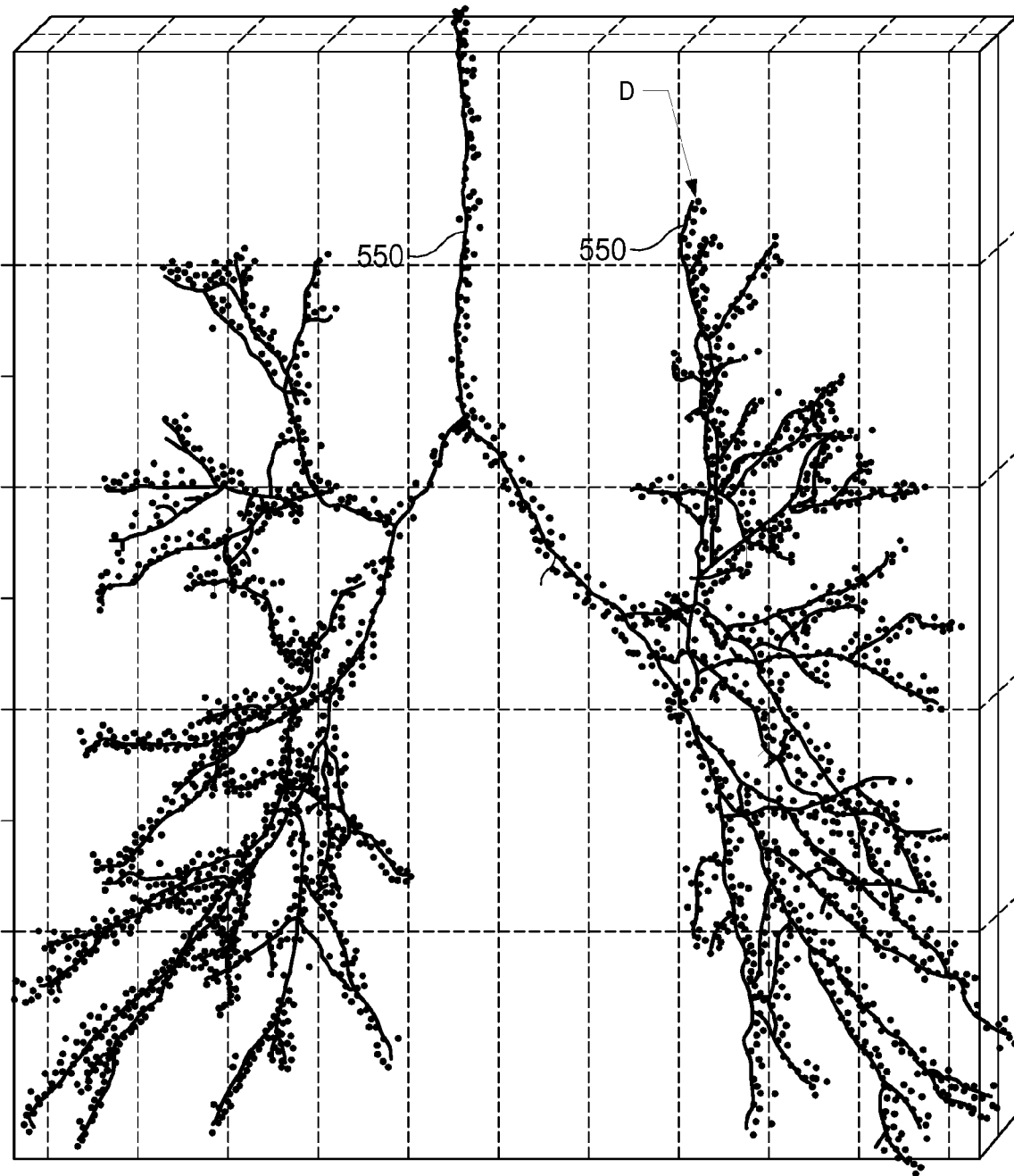

FIG. 9 illustrates an exemplary post registration alignment of two sets of points resulting from application of an exemplary registration technique.

Figure 10:
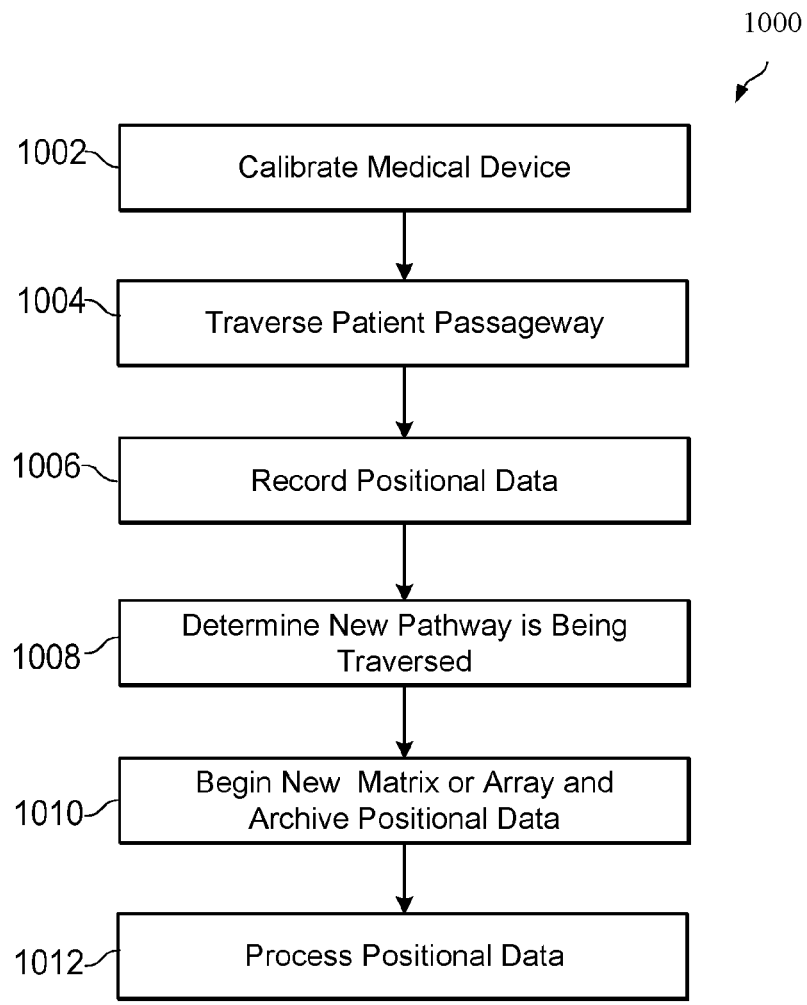

FIG. 10 illustrates a flowchart of an exemplary method for processing sensor data points to provide a more accurate passageway map.

Figure 11A:
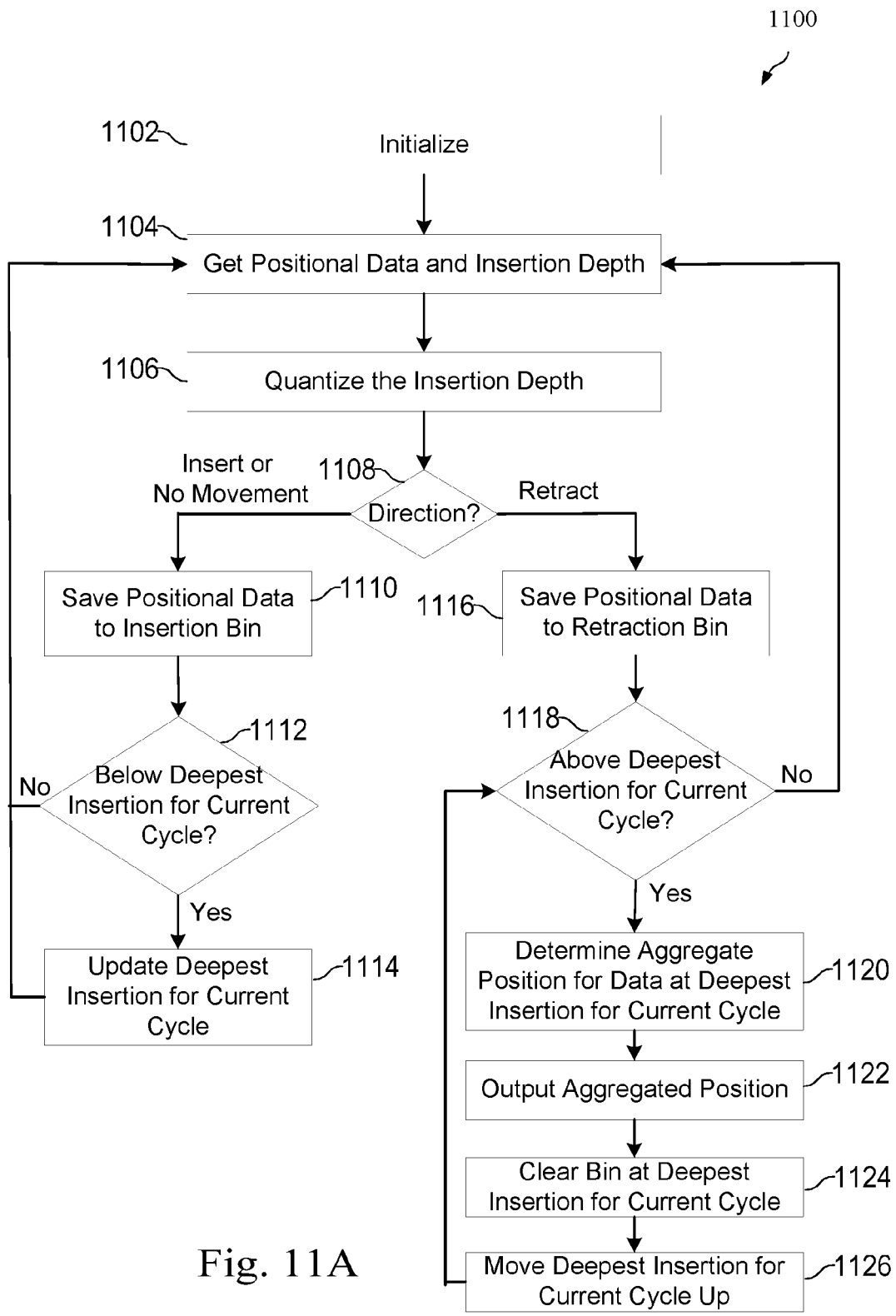

FIG. 11A illustrates a flowchart of another exemplary method for processing sensor data points to provide a more accurate passageway map.

FIG. 11B illustrates exemplary pseudo code for the method of FIG. 11A.

FIGS. 12A-12D illustrate exemplary bin structures during various stages of processing sensor data according to the method of FIG. 11A.

Figures 13A, 13B:
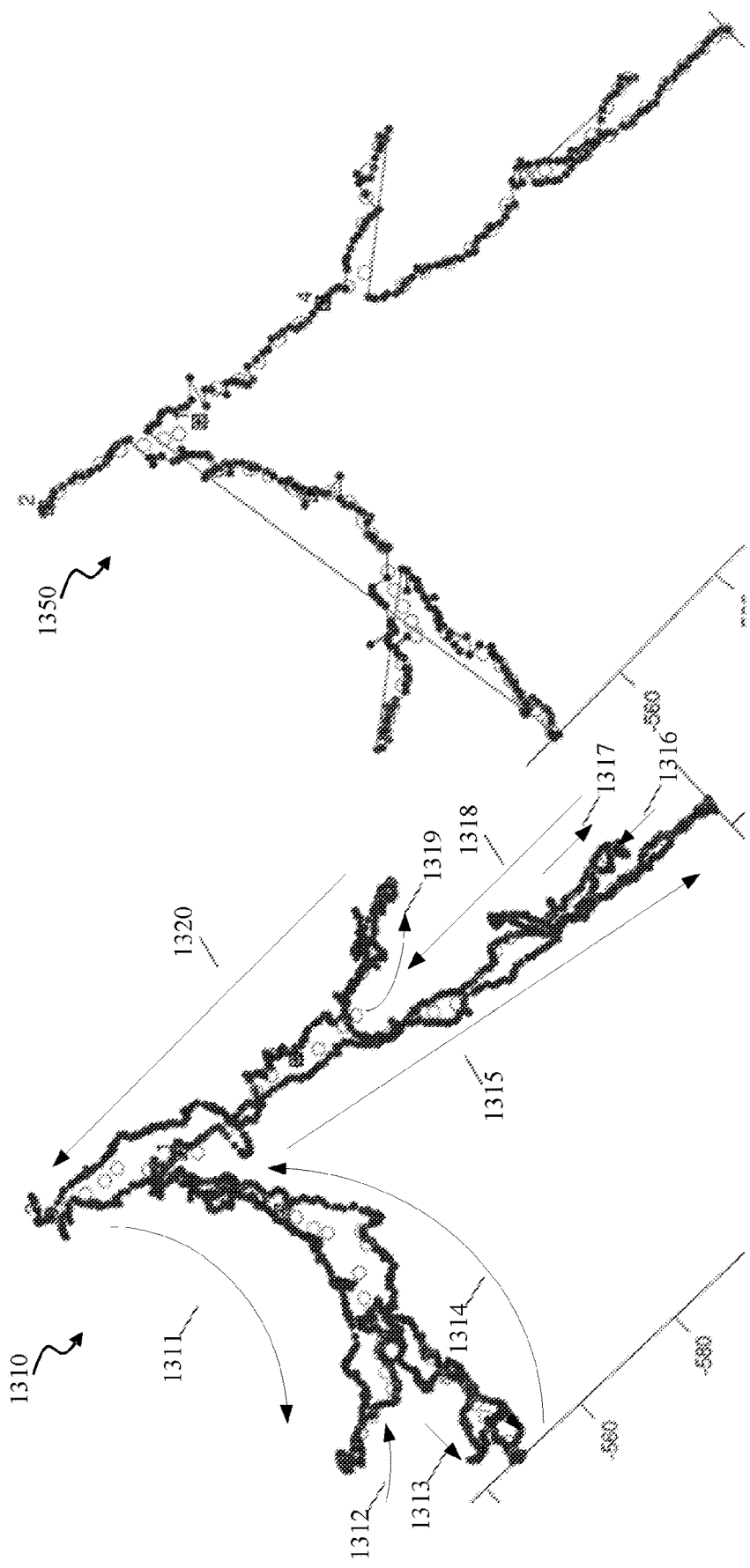

FIG. 13A illustrates an exemplary graph of raw positional data from a medical device that traversed a patient passageway.

FIG. 13B, is an exemplary graph of the positional data in FIG. 13A after the raw positional data is processed.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

This disclosure focuses primarily on embodiments where the passageways being traversed are airways in lungs. However, one of ordinary skill in the art would understand that these disclosures are equally applicable to other types of passageways that include one or more branch points. For example, other suitable anatomic passageways include vasculature, renal calyces, lymphatic vessels, and/or the like. In other examples, the passageways may correspond to non-anatomic passageways including sewer tunnels, plumbing pipes, conduits, heating ventilation and air conditioning (HVAC) ducts, mines, caves, and/or the like.

Figure 1:
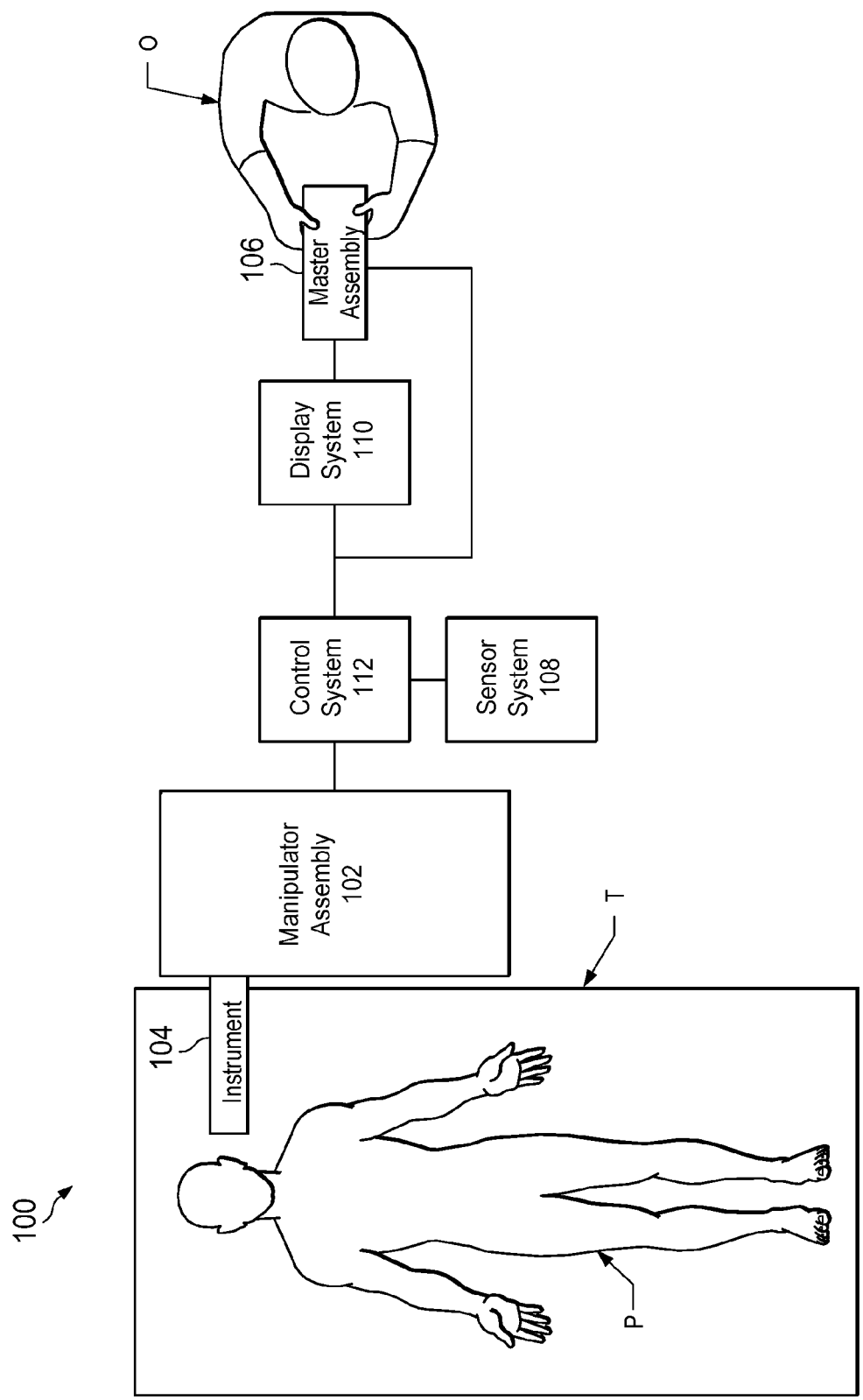
FIG. 1 is an exemplary teleoperated medical system.

FIG. 1 is an exemplary teleoperated medical system 100. In some embodiments, teleoperated medical system 100 may be suitable for use in, for example, surgical, diagnostic, therapeutic, or biopsy procedures. As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at a operator's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like.

Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one non-teleoperational manipulator assembly, more than one teleoperational manipulator assembly, and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more manipulator assemblies in various combinations.

Figure 2A:
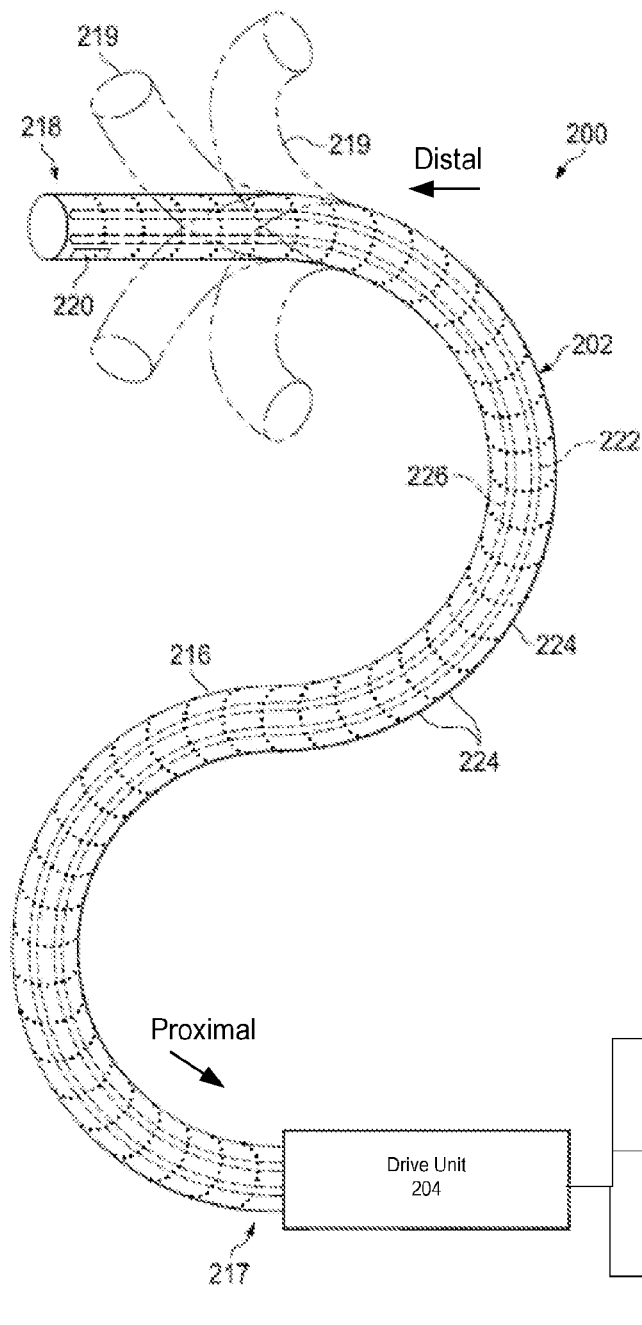
FIG. 2A illustrates an exemplary medical instrument system.

FIG. 2A is an exemplary medical instrument system 200. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as an elongate device, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering.

In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
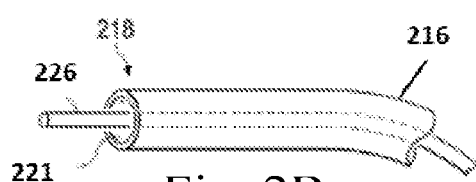
FIG. 2B illustrates an exemplary medical instrument with an extended medical tool.

Flexible body 216 includes a channel 221 sized and shaped to receive a medical instrument 226. FIG. 2B is an exemplary flexible body 216 with medical instrument 226 extended. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3:
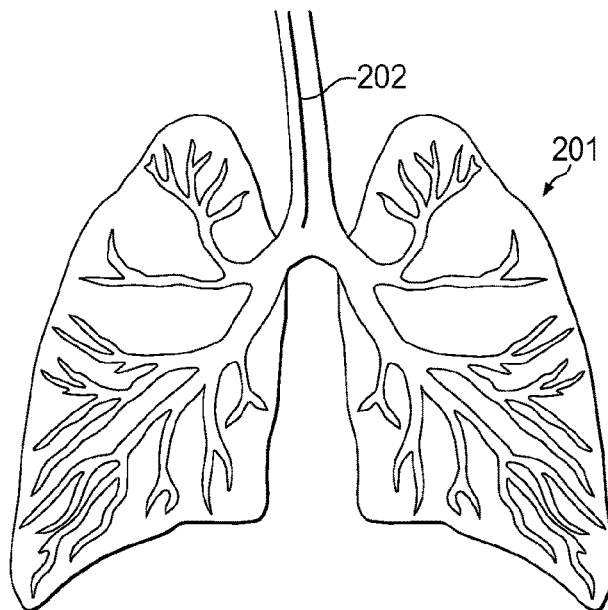
FIG. 3 illustrates an exemplary medical instrument positioned within an anatomic passageway of a human lung.

FIG. 3 illustrates an exemplary medical instrument in the form of elongate device 202 positioned within an anatomic passageway of a human lung 201. In some embodiments, elongate device 202 may be used in other passageways of an anatomy.

Figure 4:
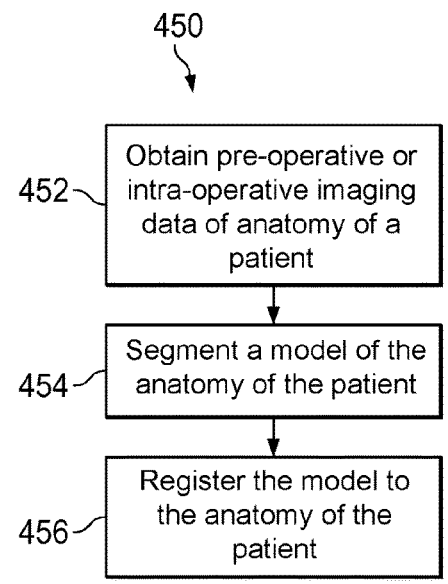
FIG. 4 illustrates a flowchart of an exemplary method to provide guidance in an image-guided surgical procedure.

FIG. 4 illustrates a flowchart of an exemplary method 450 for use in an image-guided surgical procedure. At process 452, pre-operative or intra-operative image data of the anatomy of a patient is obtained from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent human lungs 201 of FIG. 3.

At a process 454, a segmented model of the anatomy of the patient is determined. Using computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as a marching cube function, to generate a 3D surface that encloses the voxels. In some examples, the model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 456, the model is registered to the patient anatomy. In some examples, the registering may occur prior to and/or during the course of an image-guided surgical procedure on the patient. Generally, registration involves the matching of measured points to points of the model through the use of rigid and/or non-rigid transforms. Measured points may be generated using landmarks in the anatomy, electromagnetic coils scanned and tracked during the procedure, and/or a shape sensor system. The measured points may be generated for use in an iterative closest point (ICP) technique as described in further detail below. Other point set registration methods may also be used in registration processes within the scope of this disclosure.

Other registration methods for use with image-guided surgery often involve the use of technologies based on electromagnetic or impedance sensing. Metallic objects or certain electronic devices used in the surgical environment may create disturbances that impair the quality of the sensed data. Other methods of registration may obstruct the clinical workflow. The systems and methods described below may perform registration based upon ICP, or another point set registration algorithm, and the calibrated movement of a point gathering instrument with, for example, a fiber optic shape sensor, thus eliminating or minimizing disruptions in the surgical environment. Other registration techniques may be used to register a set of measured points to a pre-operative model or a model obtained using another modality.

FIGS. 5A, 5B, and 5C illustrate an exemplary application of processes in a segmentation method that generates a model of human lungs for registration. In some embodiments, the processes of FIGS. 5A, 5B, and/or 5C may correspond to portions of processes 452 and/or 454 of FIG. 4. FIG. 5A illustrates segmented model 502 of a set of anatomic passageways created from pre-operative or intra-operative imaging data. As shown, the passageways are airways of a human lung. Due to naturally occurring limitations or to limitations set by an operator, segmented model 502 may not include all of the passageways present within the human lungs. For example, relatively narrow and/or distal passageways of the lungs may not be fully included in segmented model 502. Segmented model 502 may be a three-dimensional model, such as a mesh model, that including the walls defining the interior lumens or passageways of the lungs.

Based on segmented model 502, centerline segmented model 504 may be generated as shown in FIG. 5B. Centerline segmented model 504 may include a set of three-dimensional straight lines or a set of curved lines that correspond to the approximate center of the passageways contained in segmented model 502. The higher the resolution of segmented model 502, the more accurately the set of straight or curved lines will correspond to the center of the passageways. Representing the lungs with centerline segmented model 504 may provide a smaller set of data that is more efficiently processed by one or more processors or processing cores than the data set of segmented model 502, which represents the walls of the passageways. In this way the functioning of a control system using the model, such as control system 112, may be improved. As shown in FIG. 5B, centerline segmented model 504 includes several branch points, some of which are highlighted for visibility in FIG. 5B. Branch points A, B, C, D, and E are shown at each of several of the branch points. Branch point A may represent the point in the model at which the trachea divides into the left and right principal bronchi. The right principal bronchus may be identified in the centerline segment model 504 as being located between branch points A and B. Similarly, secondary bronchi are identified by branch points B and C and between branch points B and E. Another generation of passageways may be defined between branch points C and D. Each of these generations of passageways may be associated with a representation of the diameter of the lumen of the corresponding passageway. In some embodiments, centerline model 504 may include an average diameter value of each passageway. The average diameter value may be a patient-specific value or a more general value derived from multiple patients.

In some embodiments, segmented model 502 may be used to produce segmented model 504 or another suitable model including a cloud, set, or collection of points as follows. When segmented model 502 comprises a mesh representing the internal surfaces of one or more passageways, a subset of vertices of a mesh as represented in a stored data file including segmented model 502 may be used. Alternatively, a geometric center of voxels that represent volumes or the passageways in segmented model 502 may be used. Additionally, combinations of various approaches may be used to generate a first set of points, such as segmented model 504. For example, a subset of vertices of the mesh may be used along with the geometric center of voxels from the model.

In some embodiments, centerline segmented model 504 is represented in data as a cloud, set, or collection of points in three-dimensional space, rather than as continuous lines. FIG. 5C illustrates centerline segmented model 504 as a set of points 506. Each of the points of the set of model points may include coordinates such as a set of $X_M$, $Y_M$, and $Z_M$, coordinates, or other coordinates that identify the location of each point in the three-dimensional space. In some embodiments, each of the points may include a generation identifier that identifies which passageway generation the points are associated with and/or a diameter or radius value associated with that portion of the centerline segmented model 504. In some embodiments, information describing the radius or diameter associated with a given point may be provided as part of a separate data set.

After centerline segmented model 504 is generated and stored as the set of points 506 shown in FIG. 5C, centerline segmented model 504 may be retrieved from data storage for use in an image-guided surgical procedure. In order to use centerline segmented model 504 in the image-guided surgical procedure, centerline segmented model 504 may be registered to associate the modeled passageways in centerline segmented model 504 with the patient's actual anatomy as present in a surgical environment. Use of the segmented model 504 in point set registration includes using the set of points 506 from centerline segmented model 504.

FIGS. 6A and 6B are exemplary side views of a patient coordinate space including a medical instrument mounted on an insertion assembly. As shown in FIGS. 6A and 6B, a surgical environment 600 includes a patient P is positioned on platform 602. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 600, a point gathering instrument 604 is coupled to an instrument carriage 606. In some embodiments, point gathering instrument 604 may use EM sensors, shape-sensors, and/or other sensor modalities. Instrument carriage 606 is mounted to an insertion stage 608 fixed within surgical environment 600. Alternatively, insertion stage 608 may be movable but have a known location (e.g., via a tracking sensor or other tracking device) within surgical environment 600. Instrument carriage 606 may be a component of a manipulator assembly (e.g., manipulator assembly 102) that couples to point gathering instrument 604 to control insertion motion (i.e., motion along the A axis) and, optionally, motion of a distal end 618 of an elongate device 610 in multiple directions including yaw, pitch, and roll. Instrument carriage 606 or insertion stage 608 may include actuators, such as servomotors, (not shown) that control motion of instrument carriage 606 along insertion stage 608.

Elongate device 610 is coupled to an instrument body 612. Instrument body 612 is coupled and fixed relative to instrument carriage 606. In some embodiments, an optical fiber shape sensor 614 is fixed at a proximal point 616 on instrument body 612. In some embodiments, proximal point 616 of optical fiber shape sensor 614 may be movable along with instrument body 612 but the location of proximal point 616 may be known (e.g., via a tracking sensor or other tracking device). Shape sensor 614 measures a shape from proximal point 616 to another point such as distal end or distal section 618 of elongate device 610. Point gathering instrument 604 may be substantially similar to medical instrument system 200.

A position measuring device 620 provides information about the position of instrument body 612 as it moves on insertion stage 608 along an insertion axis A. Position measuring device 620 may include resolvers, encoders, potentiometers, and/or other sensors that determine the rotation and/or orientation of the actuators controlling the motion of instrument carriage 606 and consequently the motion of instrument body 612. In some embodiments, insertion stage 608 is linear. In some embodiments, insertion stage 608 may be curved or have a combination of curved and linear sections.

FIG. 6A shows instrument body 612 and instrument carriage 606 in a retracted position along insertion stage 608. In this retracted position, proximal point 616 is at a position $L_0$ on axis A. In this position along insertion stage 608 an A component of the location of proximal point 616 may be set to a zero and/or another reference value to provide a base reference to describe the position of instrument carriage 606, and thus proximal point 616, on insertion stage 608. With this retracted position of instrument body 612 and instrument carriage 606, distal end 618 of elongate device 610 may be positioned just inside an entry orifice of patient P. Also in this position, position measuring device 620 may be set to a zero and/or the another reference value (e.g., I=0). In FIG. 6B, instrument body 612 and instrument carriage 606 have advanced along the linear track of insertion stage 608 and distal end 618 of elongate device 610 has advanced into patient P. In this advanced position, the proximal point 616 is at a position $L_1$ on the axis A. In some examples, encoder and/or other position data from one or more actuators controlling movement of instrument carriage 606 along insertion stage 608 and/or one or more position sensors associated with instrument carriage 606 and/or insertion stage 608 is used to determine the position $L_x$ of proximal point 616 relative to position $L_0$. In some examples, position $L_x$ may further be used as an indicator of the distance or insertion depth to which distal end 618 of elongate device 610 is inserted into the passageways of the anatomy of patient P.

Embodiments of the point gathering instrument 604 may collect measured points using any number of modalities, including EM sensing and shape-sensing. As the measurement points are collected from within the passageways of patient P, the points are stored in a data storage device, such as a memory. The set of measured points may be stored in a database that includes at least some, but may include all, of the measured points obtained during the procedure or immediately before the procedure. As stored in memory, each of the points may be represented by data comprising coordinates of the point, a timestamp, and/or a relative sensor position or individual sensor ID (when multiple sensors distributed along a length of the point gathering instrument 604 are used to determine the location of several points simultaneously). In some embodiments, data representing each point may also include a respiratory phase marker that indicates the respiratory phase of the patient P in which the point was collected.

FIG. 6C is an exemplary side view of patient P in a patient coordinate space including an endotracheal tube (ET) 622. As shown in FIG. 6C, elongate device 610 is inserted through ET tube 622 in order to access one or more passageways of the anatomy of patient P. In some examples, known information about a bend or curvature in ET tube 622 may optionally be used to help locate the position of distal end 618 relative to proximal point 616. In some examples, even when an exact bend or curvature of ET tube 622 is not known, general knowledge about the bend or curvature of ET tube 622 may aid it determining the position of distal end 618 relative to proximal point 616 and/or registering location data collected using elongate device 610 to model information for the passageways of the anatomy of patient P. In some examples, an interior surface 623 of ET tube 622 may optionally include a distinctive color, marking, and/or pattern that may be detectable by an imaging device, such as an endoscopic camera, located at or near distal end 618 of elongate device 610. As distal end 618 enters and/or exits ET tube 622, the change in the distinctive color, marking, and/or pattern relative to interior colors and/or patterns of the passageways may help provide useful location data for distal end 618 and/or elongate device 610.

FIG. 7 is a flowchart illustrating an exemplary method 700 of providing guidance for an image-guided surgical procedure on a patient in a surgical environment, such as surgical environment 600. And although method 700 is described generally in the context of a procedure involving the airways of lungs, it is understood that method 700 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). The method 700 is illustrated in FIG. 7 as a set of operations or processes 702-726. Not all of the illustrated processes 702-726 may be performed in all embodiments of method 700. Additionally, one or more processes that are not expressly illustrated in FIG. 7 may be included before, after, in between, or as part of the processes 702-726. In some embodiments, one or more of the processes 702-726 of method 700 may be implemented, at least in part, in the form of executable code stored on non-transitory, tangible, computer readable media that when run by one or more processors (e.g., the processors of control system 112) may cause the one or more processors to perform one or more of the processes 702-724.

At a process 702, a relative position and/or orientation of a sensor reference point along an insertion path is calibrated using a position measuring device. In some examples, the proximal point 616 may optionally correspond to the sensor reference point and point gathering instrument 604 of FIGS. 6A and 6B may optionally be used to determine a position and/or orientation of proximal point 616 as instrument carriage 606 moves from a retracted position with proximal point 616 at location $L_0$ to an inserted position with proximal point 616 at location $L_1$. The calibration of proximal point 616 includes determining the direction of the movement of proximal point 616 for each change in position measuring device 620 along axis A. In the embodiments of FIGS. 6A and 6B, where the insertion stage 608 restricts movement of instrument carriage 606 to a linear path, the calibration includes determining the motion along axis A. Using the slope of insertion stage 608 and the position along axis A, the position and orientation of proximal point 616 in surgical environment 600 is determined for each corresponding measurement of position measuring device 620. In some embodiments, where an insertion stage has a curved or otherwise non-linear shape, the calibration includes determining, based on the non-linear shape and the movement of the instrument carriage 606, the position and orientation of proximal point 616 in surgical environment 600. In some examples, calibration of proximal point 616 may optionally be determined by holding distal end 618 of elongate device 610 at a fixed position while instrument carriage 606 is moved along insertion stage 608 and shape sensor 614 is used to determine the geometrical relationship between distal end 618 and proximal point 616. By taking several readings as instrument carriage 606 is moved along insertion stage 608, the position and orientation data collected by shape sensor 614 for proximal point 616 can be correlated with data from position measuring device 620 to calibrate the position and/or orientation of proximal point 616.

At a process 704, passageways of a patient are traversed and location data along the passageways is recorded. An instrument, such as an elongate device or a flexible catheter, is inserted into and then is moved or traversed along passageways of interest. As the instrument is traversed along the passageways, the position of one or more points associated with the instrument, such as a distal end of the instrument, are monitored and recorded. In the examples of FIGS. 6A and 6B, when distal end 618 of elongate device 610 is traversed along the passageways of patient P, such as along the airways of the lungs of patient P, data from shape sensor 614 and/or one or more other sensors, such as an EM sensor, on elongate device 610 is used to determine the location of distal end 618 and/or other points associated with elongate device 610. This location data may include, and/or be processed to obtain, a set of measured points as described in further detail below. In some examples, selection of the passageways to traverse may optionally be controlled by steering distal end 618 as elongate device 610 is advanced into the passageways using movement of instrument carriage 606 along insertion stage 608. In some examples, the steering of distal end 618 may optionally be controlled via teleoperational, manual, and/or automated control, such as by using master assembly 106, to survey and obtain location data for a portion of the passageways. In some examples, the steering of distal end 618 may optionally include adjusting a roll, a pitch, and/or a yaw of distal end 618, such as is described with respect to the dashed line depictions 219 of distal end 218 in FIG. 2A. As distal end 618 of elongate device 610 is moved within the passageways, the location of the distal end 618 and/or other points associated with elongate device 610 are gathered at multiple positions of distal end 618 and/or elongate device 610. In some embodiments when the passageways correspond to airways of lungs, distal end 618 of elongate device 610 may be extended up to at least three inches or farther into the passageways. In some examples, distal end 618 of elongate device 610 may optionally be extended through or into three or more branched generations on each side of the lung. The number of generations accessible with elongate device 610 may increase as the diameter of elongate device 610 decreases and/or as the flexibility of elongate device 610 increases.

FIG. 8 illustrates exemplary location data collected by traversing airways in human lungs. As shown in FIG. 8, location data collected by process 704 is depicted by data points D. In some examples, the data points D may be stored in memory as data sets or point pools with coordinates, timestamps, sensor IDs, respiration phase information, insertion distance, and/or the like. The data points D may correspond to location data for distal end 618 and/or other points associated with elongate device 610 collected using shape sensor 614 and/or one or more other sensors as distal end 618 is advanced into and/or retracted from the passageways being traversed. In the examples of FIGS. 6A and 6B, the location of a given collected data point $D_x$ in surgical environment 600 is determined by combining information from position measuring device 620 and the shape data from shape sensor 614 and/or one or more other sensors when distal end 618 and/or some other point associated with elongate device 610 is located at the point $D_x$. In some examples, the position $L_x$ of proximal point 616 along instrument stage 608 as aided by the calibration of process 702 and data from shape sensor 614 may optionally be used to determine the location of point $D_x$. The location in the surgical environment coordinate space for the data points D becomes a reference set of location data for the passageways that can be registered with location data from a model of the passageways as is described in further detail below.

Referring back to FIG. 7, at an optional process 706, landmark data for the passageways is recorded. In some examples, one or more of the gathered data points D may correspond to one or more landmark locations within the passageways. In some examples, the gathered data points D that correspond to the one or more landmark locations may optionally be used to seed a registration process, such as an ICP process. In some examples, each of the gathered data points D that corresponds to the one or more landmark locations may be referred to as seed points. In some examples, the gathered data points D that correspond to the one or more landmark locations may be tagged with a landmark indicator when those data points D are stored in memory. In some examples, the one or more landmark locations may correspond to branch points in the passageways. In some examples, when the passageways are airways in lungs, the one or more landmark locations may correspond to carinas within the lungs.

In some examples, designation of the data points D as corresponding to the one or more landmark locations may occur as a result of input from an operator, such as operator O, and/or through one of more other approaches and/or automated algorithms. In some examples, the operator may designate data points D as corresponding to the one or more landmark locations by pressing a button, a pedal, a lever, issuing a command recognizable with voice recognition, and/or the like and/or activating an appropriate input control on a master assembly, such as master assembly 106. In some examples, the operator may navigate the distal end of the elongate device to a point in proximity to one of the landmark locations and initiate physical contact between the distal end and a wall of the passageways. In some examples, a torque sensor and/or an encoder for an actuator controlling the distal end may register resistance and/or a force against the distal end due to the contact with the wall of the passageway and trigger the tagging of the current location of the distal end as a landmark location. In some examples, a touch sensor, such as a capacitive and/or a Hall effect sensor, may be positioned near the distal end of the elongate device to provide an indication when the distal end is close to or in contact with the wall of the passageways and trigger the tagging of the current location of the distal end as a landmark location.

In some examples, when the distal end of the elongate device is passed through an ET tube, such as ET tube 622, a known bend or curvature of the ET tube may aid in the identification of one or more of the landmark locations. In some examples, even when the bend or curvature in the ET tube is not precisely known, the bend or curvature may be sufficiently distinctive to be identified as corresponding to a specific region of the passageways, such as the upper respiratory track and trachea because a more proximal portion of the elongate device at a proximal end of the ET tube forms a nearly 90° angle with respect to a more distal portion of the elongate device at a distal end of the ET tube. Based on pose information of the proximal point of the elongate device and the curvature of the ET tube, which may be easily identified using the shape sensor, the trachea of the patient may be identified and used as one of the landmark locations. In some examples, detection and location of the distal end of the ET tube, such as by detecting the end of a distinctive color, marking, and/or pattern of an interior surface of the ET tube, may further aid in identifying a landmark location within the trachea of the patient.

According to some embodiments, when the orientation of the patient relative to the proximal point of the elongate device is known, navigation of the distal end of the elongate device to the left or the right may help identify one or more landmark locations associated with the left and/or right primary bronchus. In some examples, data from the shape sensor and/or other sensor may optionally be used to identify the roughly right angle between the proximal end and the distal end of the ET tube created by the curvature of the ET tube, with the distal end of the ET tube identifying a possible landmark location within the trachea of the patient. In some examples, the roughly right angle may optionally be used to identify a first plane that bisects the anatomy of the patient into right and left halves. As the distal end is further steered into either the left or right primary bronchus, a second angle defining a second plane may be identified, which is roughly orthogonal to the first plane. The orientation of the first and second planes may then be used to determine one or more additional landmark locations.

At a process 708 model information for the passageways is received. In some examples, pre-operative and/or intra-operative images of the passageways, such as the images obtained using process 542, may be used to construct the model of the passageways. In some examples, the model of the passageways may be generated by segmenting the pre-operative and/or intra-operative images using processes 454. In some examples, the model information for the passageways may correspond to the centerline segmented model 504 as described in FIG. 5C.

At an optional process 710, an initial seed transformation between the landmark data and the model information for the passageways is determined. According to some embodiments, use of a suitable seed transformation for close point registration algorithms, such as ICP often result in better registration and/or faster convergence for the close point algorithm. In some examples, the transformation that maps between the landmark locations identified in the landmark data during process 706 and the corresponding locations in the model information received during process 708 often provides a good seed transformation for close point registration between the location data collected during process 704 and the model information received during process 708. In some examples, the initial seed transform may optionally be a rigid transform in which each of the data points D for the landmark locations are transformed by the same coordinate transformation that maps positions and orientations from a coordinate system of the location data collected during process 704 and a coordinate system for the model information received during process 708. In some examples, the initial seed transformation may optionally be a non-rigid transformation where each of the data points D for the landmark locations are transformed by different coordinate transformations. In some examples, the initial seed transformation may be modeled as a homogenous transform that can translate and/or rotate 3D points from one coordinate system to another. In some examples, multiple initial seed transformations determined using different landmark data and/or different landmark locations may optionally be compared with the initial seed transformation having the smallest error when mapping between the coordinate system of the location data collected during process 704 and the coordinate system for the model information received during process 708 being selected as the initial seed transformation. In some examples, the first and second planes determined during process 706 may optionally be used to determine the initial seed transformation.

At an optional process 712, the initial seed transformation is applied to the recorded location data. Using the rigid or non-rigid transformation determined during process 710, the location data collected and recorded during process 704 is transformed to place the points in the location data in closer alignment with corresponding points in the model information received during process 708. In some examples, when the initial seed transformation is a homogeneous transformation, the transformation of the location data is accomplished by applying the initial seed transformation to each of the points in the location data using matrix multiplication.

At a process 714, the location data recoded during process 704 is registered to the model information received during process 708. Process 714 is shown as an iterative process that includes repeated application of processes 716-722 until convergence between the location data and the model information is obtained. In some examples, the iterative processes of process 714 correspond to the ICP registration technique. FIG. 9 illustrates an exemplary post registration alignment of two sets of points resulting from application of process 714 to the location data as collected and shown in FIG. 8. In some examples, process 714 may be performed in conjunction with process 704. For example, while location data is being collected during process 704, location data points may be simultaneously matched with model information.

At a process 716, points in the location data are matched to points in the model information. Transformation of the points in the location data using the initial seed transformation during process 712 and/or by the transformation of process 720 as described further below typically brings the points in the location data into better positional and/or rotational alignment with corresponding points in the model information. However, because initial iterations to bring the points in the location data in alignment with corresponding points in the model information do not always identify the correct correspondence between the points in the location data and the points in the model information, rematching to update the correspondence is performed. Each of the points in the location data, as transformed, is matched to a point in the model information that is closest to the point in the location data. In some examples, the closest point in the model information may be determined by iterating through each of the points in the model information and finding the point that has a shortest Euclidean distance to the point in the location data being matched. In some examples, other techniques, such as KD trees and/or the like may optionally be used to more efficiently perform the matching. In some examples, some matches may be discarded based on a maximum distance threshold determination, a maximum angle threshold determination, and/or other metrics employed to filter out matches that are not deemed to be reliable enough or "close" enough for inclusion in the transformation determined during a process 718 as is described further below.

At the process 718, a further transformation is determined. Based on the matching of process 716, the further transformation identifies an additional transformation to the location data to bring the location data into further alignment with the model information. In some examples, the further transformation determines a displacement and/or rotation, such as in the form of a homogenous transformation, which would best bring the matched points into alignment. In some examples, the further transformation is determined by computing an overall and/or an aggregated offset in position and orientation between the points matched during process 716. In some examples, the further transformation may be limited such that a maximum offset and/or a maximum rotation is applied during any iteration of process 714. In some examples the maximum offset and/or the maximum rotation may optionally be scaled based on a number of iterations of process 714 that have been performed.

At a process 720, the further transformation is applied to the location data. Using the further transformation determined during process 718, the location data as transformed by process 712 and/or prior applications of process 720 is further transformed to place the location data in closer alignment with the points in the model information received during process 708. In some examples, when the further transformation is a homogeneous transformation, the further transformation of the location data is accomplished by applying the further transformation to each of the points in the location data using matrix multiplication.

At a process 722, the convergence of the registration technique is evaluated. In some examples, error measures between the locations of the points in the location data and the locations of the points in the model information are computed that assess an overall difference between the location data as transformed and the model information. When the error measures in aggregate are greater than a threshold value, additional iterations of processes 716-722 are repeated until the overall error measures fall below the threshold value. A result of this process is illustrated in FIG. 9 showing how multiple iterations of processes 716-722 are able to bring the location data as represented by points D in FIG. 8 into alignment with the points in anatomic model information 550. In some examples, a number of iterations to converge between FIG. 8 and FIG. 9 may vary based on differences between the model information and the actual point locations in the location data, the convergence threshold, and/or the like.

In some embodiments, the progression of processes 716-722 may optionally be displayed to an operator, such as operator O, by displaying images similar to FIGS. 8 and 9 on a user interface display. In some examples, the operator may optionally monitor the registration to determine when adequate convergence is achieved. In some examples, the registration of processes 716-722 may optionally be repeated during a surgical procedure such as at regular intervals, as additional location data is obtained, when the patient is moved, and/or the like.

After the registration is complete, an image-guided surgical procedure may, optionally, be performed. In some examples, the model information may identify one or more intervention sites and/or targeted locations in the anatomy of the patient to which a targeted procedure is to be applied. In some examples, a composite transformation including the initial seed transformation determined during process 710 and each of the further transformations determined during process 718 may be used to map current location data for the distal end of the elongate device to a corresponding location in the model information to aid the operator in planning and/or executing a motion plan to move the distal end of the elongate device from its current location to one of the targeted locations. As shown in FIG. 7, the image-guided surgical procedure may correspond to optional processes 724 and 726.

At the optional process 724, a current location of the distal end of the elongate device is determined. In some examples, the location of the proximal point and data from the shape sensor may be used to determine the current location of the distal end of the elongate device where a surgical instrument can be applied to the anatomy of the patient by inserting the surgical instrument through the elongate device. In some examples, other sensors, such as the EM sensor may optionally be used to determine the current location of the distal end of the elongate device.

At the optional process 726, the distal end of the elongate device is located in the model information. Using the composite transformation determined by processes 702-722, the current location of the distal end of the elongate device determined during process 724 may be transformed so that the location of the distal end of the elongate device, and thus the surgical instrument may be determined relative to the model information. Once the location of the distal end of the elongate device is known within the passageways as described in the model information, it is possible for the operator and/or an automated system to plan and/or execute a motion plan to deliver the surgical instrument to one of the targeted locations. As the plan is executed, processes 724 and 726 may be repeated to continually update the current location of the distal end of the elongate device and the motion plan.

As discussed above and further emphasized here, FIG. 7 is merely an example which should not unduly limit the scope of the claims. One of ordinary skill in the art would recognize many variations, alternatives, and modifications. In some embodiments, the transformation of processes 712 and/or 720 may be applied in different ways. In some examples, the initial seed transformation and/or the further transformation may optionally be defined to transform the points in the model information so that they are in closer alignment with the points in the location data with the initial seed transformation and/or the further transformation being applied to transform the model information rather than the location data. In some examples, the initial seed transformation and/or the further transformation may optionally be divided into separate transformations designed to transform both the location data and the model information toward a common coordinate system.

As a medical device (e.g., elongate device 610 of FIG. 6, medical instrument system 200 of FIG. 2A, medical instrument 104 of FIG. 1, and/or the like) traverses the anatomic passageways of a patient, the location of the medical device within the anatomic passageways may deviate from the center line of the passageways. As such, when the medical device is used to record location data to map the passageways, the location data may have perturbations from the actual passageways.

One cause of these deviations may be the size of the passageways. For example, if the inner diameter of the passageway is greater than the outer diameter of the medical device, the medical device may move laterally within the passageway. Thus, as the device is inserted, it may rest on one side of the passageway at an insertion distance $L_x$. As the device is retracted, it may rest on the opposite side of the passageway at the insertion distance $L_x$. Another cause of the deviations may be kinks or other deformations in the medical device that develop as it is pushed through the passageways. Sensor data captured while these deviations occur may, once displayed, imply curvatures in a passageway or additional passageways that do not actually exist.

Similarly, other causes of deviations may occur due to the medical device exhibiting a force on the passageways. The medical device may press against a bend in a passageway, moving the passageway from its normal resting place. This may cause data captured during an insertion to be slightly different from data captured during a retraction. Other sources of positional data error may be from sensor noise and/or general inaccuracies of the sensor device.

Although the ideal data mapping points would be a centerline model as shown in FIG. 5C, the actual sensor data tends to be much noisier, as shown in FIG. 8. Therefore, it would be beneficial if a system and/or method were able to filter and/or develop more accurate data points for mapping passageways.

FIG. 10 illustrates an exemplary method 1000 for processing sensor data points to provide a more accurate passageway map. And although method 1000 is described generally in the context of a procedure involving the airways of lungs, it is understood that method 1000 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). In some examples, method 1000 takes advantage of and/or accounts for repeated traversals that one or more sensors may make during a procedure. In some examples one or more of processes 1002-1012 may replace, be the same as, and/or be performed in addition to processes 702-726 of FIG. 7. In some embodiments, one or more of the processes 1002-1012 of method 1000 may be implemented, at least in part, in the form of executable code stored on non-transitory, tangible, computer readable media that when run by one or more processors (e.g., the processors of control system 112) may cause the one or more processors to perform one or more of the processes 1002-1012.

At process 1002, the system may calibrate the relative position/orientation of a sensor reference point along an insertion path. In some examples, process 1002 may be substantially similar to process 702 of FIG. 7.

At process 1004, the system may begin traversing into a passageway. In some examples, the insertion may be controlled by a user, such as operator O, manually or teleoperatively guiding the medical device through the passageways of a patient. In some examples, the insertion may be automated based on preprogrammed insertion paths and/or self-guided insertion using artificial intelligence.

At process 1006, the system may record positional data for one or more points of the medical device, such as a distal end and/or other points on the medical device. This positional data may be a combination of different sensor data, such as direction and insertion distances from an actuator controlling the movement of the medical device as discussed in FIG. 6 above, and/or three dimensional positional coordinates for one or more sensors within the medical device. For example, each sensor record i for a point of the medical device may include three-dimensional position coordinates in the surgical coordinate space ($X_i$, $Y_i$, $Z_i$), an I/O sensor value for an insertion axis degree of freedom (e.g., from position measuring device 620), and/or an insertion axis direction value indicating whether the medical device is moving forward, backward, or is stationary (e.g., value of +1 for moving forward along the insertion axis, value of −1 for moving backward along the insertion axis, or a value of 0 for stationary). In some examples, the directional value indicating whether the medical device is moving forward, backwards, or is stationary may be determined from an indication provided by the I/O sensor. In some examples, the directional value may be determined by the system from the change in I/O sensor value and/or other sensor positional information. In an alternative example, the directional value may be determined by a user input through a user interface or control console indicating to the system that the direction or stationary movement of the medical device whether it be manually or teleoperatively controlled.

In some examples, the system may quantize and track the insertion distance of the medical device (e.g., using position measuring device 620), such that the system may match positional data from the sensor during an insertion along a path with positional data from the sensor during a retraction along the same path.

Insertion and retraction positional data may be similar at the same insertion distances if the medical instrument closely tracks the passageway. For example, if the outer diameter of the medical instrument is close to the inner diameter of the passageway lumen, the insertion and retraction positional data may be a closer match than if the medical instrument has an outer diameter that is much smaller than the inner diameter of the passageway lumen.

Optionally, in some examples, the quantized distance may be set to be equal to the distance between a plurality of sensors within the medical device or a whole number multiple of that distance. In this manner, as the insertion is increased or decreased by a quantized amount, each sensor provides positional data in the position of an adjacent sensor prior to the change in insertion. For example, there may be a first sensor at a distal end of the medical device and a second sensor behind the first sensor. Because the quantized distance value is set to the distance between the first and second sensors, when the medical device is advanced by the quantized amount, the second sensor may be placed in the same or approximately the same location of the first sensor prior to the advancement.

In some examples, the system may have a continuous insertion and retraction distance and the system may quantize the distances based on the insertion and/or retraction distance. For example, the system may be configured to round up and/or down to a nearest quantized insertion distance or unit for each positional data point and insertion distance. For example, if an insertion distance were to be 1.1, the system may round down to a quantized insertion distance of 1. Similarly, if the insertion distance were to be 1.5, the system may round up to a quantized insertion distance of 2. Additionally, based on the direction of the insertion, either determined from an indicator from the actuator or from the change in position, the distance information may be tagged with a directional indicator. The indicator may be a negative or positive value. In some examples, the tag may be separate value associate with the insertion distance, such as +1 for insertion, −1 for retraction, and 0 for stationary.

In some examples, each positional sensor coordinate value may be associated with a quantized insertion distance. In some examples, the positional data may be stored in a matrix or array wherein each cell of the matrix or array may represent an insertion distance, sensor reading order, and/or passageway. The system may determine which cell each data point is placed in based on positional data received from the sensor positions from the positional sensor, the insertion depth determined from the actuator or I/O sensor, the direction of movement determined from the actuator I/O sensor, and/or the operator. In some examples, the system may also determine the cell based on other information such as time stamps, whether the data is a duplicate insertion distance, direction movement information of the medical device, and/or the like.

Optionally at process 1008, the system may determine that a new passageway is being traversed. When mapping anatomic passageways, such as that of a patient's lungs, a medical device may be inserted to the end of a passageway or where the passageway becomes too narrow to further traverse and then may be retracted to a fork position and then inserted into another passageway. In some examples, an operator of the system may provide an indication when a new passageway is being explored and/or when a passageway is exited. Such an indication may be through one or more control devices and/or interactions with a graphical user interface.

In some examples, the system may be configured to automatically determine when a new passageway is being traversed. For example, the system may determine a new passageway is being traversed when the medical device is retracted to a landmark and/or fiducial marker and then reinserted. In some examples, the system may determine that a new passageway is being traversed when, after a retraction and another insertion, new positional data for a quantized insertion distance is beyond a threshold deviation from the previous positional data for the same quantized insertion distance.

In some examples, the distal end of the medical device may be controllable by an operator to flex in one direction or another. In some examples, a combination of data along with the flex control of the medical device may be used to determine whether a new passageway is being traversed. For example the system may receive data that at a first insertion distance during an insertion, the distal end of the device was controlled by an operator towards a first direction. The system may also receive another data point for the same insertion distance after a retraction wherein the operator flexed the distal end of the medical device in a different direction than the first direction before another insertion.

The system could determine based on this data that the medical device is traversing a new passageway.

Based on the above methodologies, the system can determine whether the medical device has retracted out of one passageway and begun insertion into another passageway. In some examples, the system may use a combination of one or more of these methods to determine whether a new insertion path is being traversed.

Optionally, at process 1010, in response to determining that a new passageway is being traversed at process 1008, the system may store positional data for the new passageway in a new separate data matrix and/or array. The data captured for the previous passageway may be archived and/or provided a unique identifier for identifying the passageway. In some examples, the data archived may be for a partial passageway. For example, the medical device may be inserted a distance of 5 units, retracted a distance of 3 units, and then be inserted for a distance of 2 units along another path. In this example, the medical device has not retracted back the first two units. In such an example, the positional data collected when the medical device was inserted 3 units past the first two units and then retracted may be archived and a new data array or matrix may be created for the positional data collected for the next two units of insertion, assuming this is determined to be for another path. In some examples, instead of a new data array or new matrix, the data may be placed in a new row/column or other dimension of a matrix and/or array. In some examples, because the first two units have not been retracted yet, the position data collected during that insertion distance may not be archived until the medical device retracts back through those original insertion units.

At process 1012, the system may process the positional data captured during the insertion along the path and the positional data captured during the retraction along the path in order to provide a more accurate passageway mapping.

In some examples, the system may aggregate, such as by averaging, the positional data captured for each separate quantized insertion distance. For example, positional data captured at a quantized insertion distance of 1 may be averaged with other positional data captured at the quantized insertion distance of 1 for the same passageway. In some examples, this may be positional data captured at that quantized insertion distance during insertion of the medical device and the positional data at that quantized insertion distance during retraction of the device.

In some examples, the average may be for multiple positional data points that were rounded to that quantized insertion point. For example, positional data captured at insertion distances of 0.5, 0.6, 0.7, 0.8, 0.9, 1, 1.1, 1.2, 1.3, and 1.4 may be associated with quantized position of 1, and the positional data may be aggregated to determine a more accurate position for the passageway at the insertion distance of 1.0.

In some examples, the positional data points collected during both the insertion and retraction directions within a same path may be assigned a common label used during registration (such as during registration process step 714) to match common labeled positional data points to model points found in a corresponding common passageway in a model and/or image. In this manner, a first positional point collected during insertion along a path is known to be in the same passageway as a second positional point collected during a retraction along the same path because a medical device cannot retract along a different passageway than initially entered. Accordingly, the common label can be used as additional matching criteria when matching positional data points to model data points. As previously described in reference to process 716 of method 700, positional points may be iteratively matched to closest points in a model, using in one example a shortest Euclidean distance between the positional points and the model points. In some examples, additional matching criteria may be provided using a common label such that, for example, if a first model point is closest to a first positional point but does not have a common label with the first positional point, the first model point and the first positional point are not located within the same passageway and should not be matched. In some examples, the first positional point may instead be matched to a second model point which has been assigned with the common label indicating it is within a common passageway.

In some examples, the system may include positional data from other sensors that also captured positional data at those same equivalent quantized insertion distances. For example, if a first sensor is one quantized distance behind a second sensor, the positional data of the second sensor at insertion distance 2 could be averaged with positional data of the first sensor at insertion distance 1.

In this manner, the errors in the positional data due to passageways significantly larger than the instrument, sensor noise, and/or forced movement of the passageways may be minimized through the aggregated positional data. As such, the mapped passageways using the sensor positional data may be smoothed out to create a more linear model of the passageways.

In some examples, process 1012 may be performed in response to a request to filter or smooth data points when displaying the passageway using the positional data. In some examples, process 1012 may be performed in response to the system determining that a new passageway is being traversed.

In some examples, the system may archive the aggregated positional data at process 1010 separately from the data actually recorded at process 1006. In this manner, the original raw data is preserved. Furthermore, both the raw and aggregated positional data could be displayed on a graphical user interface for comparison. In some examples, the system may display the raw positional data and processed positional data using a color-coded format. In this manner, a viewer viewing the passageway map may be able to differentiate between the different types of positional data and make a determination on which the viewer prefers or considers more accurate.

In some examples, some positional data points may be assigned different weights. For example, insertion positional data may generally be noisier than retraction positional data. As such the system may provide a higher weight to the positional data during retraction when performing the aggregation.

FIG. 11A illustrates a flowchart of another exemplary method 1100 for processing sensor data points to provide a more accurate passageway map. And although method 1100 is described generally in the context of a procedure involving the airways of lungs, it is understood that method 1100 is applicable to other anatomical passageways (e.g., blood vessels, ducts, calyces, and/or the like), anatomical passageways in a non-surgical context (e.g., passageways of cadavers, simulated anatomical structures, and/or the like), veterinary passageways, and/or non-medical passageways (e.g., pipes, conduit, ducts, corridors, wells, caves, mines, and/or the like). FIG. 11B illustrates exemplary pseudo code for method 1100 of FIG. 11A. In some examples, method 1100 takes advantage of and/or accounts for repeated traversals that one or more sensors may make during a procedure. In some examples one or more of processes 1102-1126 may replace, be the same as, and/or be performed in addition to processes 702-726 of FIG. 7 and/or processes 1002-1012 of FIG. 10. In some embodiments, one or more of the processes 1102-1126 of method 1100 may be implemented, at least in part, in the form of executable code stored on non-transitory, tangible, computer readable media that when run by one or more processors (e.g., the processors of control system 112) may cause the one or more processors to perform one or more of the processes 1102-1126.

At process 1102, initialization for the method takes place. In some examples, the medical device used to traverse the passageways of the patient may be initially positioned in the passageways. In some examples, a position and/or orientation of a sensor reference point along an insertion path (e.g., position $L_0$) may be calibrated. Initialization further includes recording an initial insertion depth for the medical instrument as a baseline of the deepest insertion point for the medical instrument for a current insert/retract cycle. In some examples, the initial insertion depth may be quantized to identify a deepest bin that contains positional data as is described in further detail below. In some examples, quantizing the initial insertion depth includes dividing the initial insertion depth by a bin size (i.e., a distance between a deepest depth quantized to the bin and a shallowest depth quantized to the bin) and rounding the result to the nearest whole number or alternatively recording the initial insertion depth as a baseline and setting the deepest bin to zero. For example, an initial insertion depth of 0.5, 0.6, 0.7, 0.8, 0.9, 1, 1.1, 1.2, 1.3, or 1.4 may be associated with quantized insertion depth of 1 when the bin size is 1. The bin size controls how close together in insertion depth two or more positional data values are before they are aggregated by the processing of method 1100. In some examples, the bin size is selected based on a desired precision of the resulting passageway positional data with a larger bin size generally resulting in fewer, more widely spaced positional values with lower precision. In some examples, the bin size may be optionally configured based on an accuracy of the medical device, a size of the passageways, a preference of a user, and/or the like.

At process 1104, current positional data and an insertion depth for the medical instrument are determined as the medical instrument is traversed through the passageways. In some examples, the current positional data includes a three-dimensional location of a sensor, a fiducial marker, and/or the like within a surgical coordinate system $(X_i, Y_i, Z_i)$. In some examples, the positional data may correspond to a location of a distal end of shape sensor 222 and/or 614, an EM sensor of tracking system 230 within a surgical coordinate space, and/or the like. In some examples, the insertion depth may be determined using an I/O sensor, such as a location of proximal point 616 relative to $L_0$ as instrument body 612 is moved along instrument carriage 606. In some examples, collection of the current positional data and insertion depth may be triggered periodically by a timer, by manual triggering by a user, and/or based on a detected condition of the medical device.

At process 1106, the current insertion depth received during process 1104 is quantized based on the bin size. In some examples, when the initial insertion depth is used as a baseline, the quantized insertion depth is determined by subtracting the initial insertion depth from the current insertion depth, dividing the difference by the bin size, and rounding to the nearest whole number. In some examples, when an insertion depth of zero is used as a baseline, the quantized insertion depth is determined by dividing the current insertion depth by the bin size and rounding to the nearest whole number.

At process 1108, the insertion direction of the medical instrument is determined. During process 1108 it is determined whether the medical instrument is being inserted, being retracted, or is not moving (neither being inserted nor retracted). In some examples, the insertion direction may be coded as +1 for insertion, 0 for no movement, and −1 for retraction. In some examples, the insertion direction may be determined by taking the sign (e.g., using the signum function) of the difference between the current insertion depth and the previous insertion depth. In some examples, the insertion direction may be determined based on a velocity of the medical instrument, such as the velocity of instrument stage 608. In some examples, the insertion direction may be determined by sensing a user input of a control on a user interface, control console, and/or the like that is used to control insertion, retraction, or no movement of the medical instrument as it is traversed through the passageways either manually and/or teleoperatively. When the insertion direction is determined to be insertion or not moving, the current positional data is further processed beginning with process 1110. When the insertion direction is determined to be retraction, the current positional data is further processed beginning with process 1116.

At process 1110, the current positional data received during process 1104 is saved in an insertion bin corresponding to the quantized insertion depth determined during process 1106. The insertion bin is one of a collection of insertion bins that may be implemented using any suitable data structure that is indexible by the quantized insertion depth. For example, the collection of insertion bins may be implemented as an array, vector, map, and/or the like that stores variably sized collections of positional data (e.g., the $(X_i, Y_i, Z_i)$ of the current positional data). In some examples, each of the variably sized collections may correspond to a set, a vector, a linked list, and/or the like. The collections are variably sized to account for the possibility that zero, one, two, three, or even more sampled positional data values may be stored in the insertion bin at the quantized insertion depth depending upon how long and/or how frequent the current position of the medical device is sensed before the insertion depth of the medical device is quantized into the a deeper insertion bin.

At process 1112, it is determined whether the quantized insertion depth determined during process 1106 is below the deepest quantized insertion depth for the current insertion/retraction cycle. Method 1100 keeps track of the deepest insertion point of the current insert/retract cycle of the medical device by keeping a record of the deepest insertion bin into which positional data has been recorded by process 1110. When the quantized insertion depth is not below the deepest quantized insertion depth for the current insertion/retraction cycle (i.e., the positional data recorded during process 1110 is recorded in an insertion bin that already holds other positional data), another current positional data and insertion depth are retrieved by returning to process 1104. When the quantized insertion depth is below the deepest quantized insertion depth for the current insertion/retraction cycle (i.e., the positional data recorded during process 1110 is recorded in an empty insertion bin), the deepest quantized insertion depth for the current insertion/retraction cycle is updated using process 1114.

At process 1114, the deepest quantized insertion depth for the current insertion/retraction cycle is updated by recording the quantized insertion depth as the deepest quantized insertion depth for the current insertion/retraction cycle. After the deepest quantized insertion depth for the current insertion/retraction cycle is updated, another current positional data and insertion depth are retrieved by returning to process 1104.

At process 1116, the current positional data received during process 1104 is saved in a retraction bin corresponding to the quantized insertion depth determined during process 1106. The retraction bin is one of a collection of retraction bins that are managed similarly to the collection of insertion bins, but are kept separately so that positional data obtained during insertion may be processed separately from positional data obtained during retraction. Both the collection of retraction bins and the collection of insertion bins are indexed similarly so that positional data obtained during retraction and positional data obtained during insertion may related to each other as the positional data is further processed.

At process 1118, it is determined whether the quantized insertion depth determined during process 1106 is above the deepest quantized insertion depth for the current insertion/retraction cycle. When the quantized insertion depth is above the deepest quantized insertion depth for the current insertion/retraction cycle, this indicates that there is at least one pair of insertion and retraction bins below the quantized insertion depth that contain previously recorded positional data that is ready to be output. This previously recorded positional data is further processed to prepare the collections of insertion bins and retraction bins for additional positional data that may correspond to positional data for a different branch in the passageways that should not be aggregated with the previously recorded positional data because positional data aggregated from different passageways would not generally be indicative of a location of the passageways. When the quantized insertion depth is not above the deepest quantized insertion depth for the current insertion/retraction cycle, another current positional data and insertion depth are retrieved by returning to process 1104. When the quantized insertion depth is above the deepest quantized insertion depth for the current insertion/retraction cycle, the positional data in the insertion and retraction bins below the quantized insertion depth are processed beginning with process 1120.

At process 1120, the positional data in the insertion and retraction bins corresponding to the deepest quantized insertion depth for the current insertion/retraction cycle are aggregated together. In some examples, aggregating the positional data includes aggregating the positional data in the insertion bin at the deepest quantized insertion depth for the current insertion/retraction cycle to form a first aggregation value, aggregating the positional data in the retraction bin at the deepest quantized insertion depth for the current insertion/retraction cycle to form a second aggregation value, and aggregating the first and second aggregation values to obtain an aggregate positional value corresponding to the insertion depth of the deepest quantized insertion depth for the current insertion/retraction cycle. In some examples, an aggregation such as an average, an arithmetic mean, a mode, and/or the like may be used to determine the first aggregation value, the second aggregation value, and/or the aggregate positional value. Initially aggregating the positional data obtained during insertion separately from the positional data obtained during retraction may reduce the effects caused by having significantly more positional data points from insertion than from retraction, or vice versa. In some examples, special cases may occur when either the insertion bin or the retraction bin at the recorded deepest bin depth are empty (which may occur, for example, during a particularly fast insertion or retraction). In either of those cases the corresponding first or second aggregation value is not determined and the other of the first and second aggregation values becomes the aggregate positional value. If both the insertion bin and the retraction bin at the recorded deepest bin depth are empty, processes 1120 and 1122 are skipped. Alternatively, when a bin is empty, its positional value can be determined by interpolating the positional value of the two neighboring bins in the same moving direction (i.e., insertion or retraction).

At process 1122, the aggregate positional value determined during process 1120 is output as a sensed position within the passageways. The aggregated positional value is output by providing it to a method that relies on sensed and/or recorded passageway locations, such as those obtained and recorded during process 704 of method 700.

At process 1124, the positional data in both the insertion bin and the retraction bin corresponding to the deepest quantized insertion depth for the current insertion/retraction cycle is cleared. Once the positional data in the insertion and retraction bins corresponding to the recorded deepest quantized insertion depth for the current insertion/retraction cycle are aggregated during process 1120 and output during process 1122, they are no longer needed and can be deleted.

At process 1126, the deepest quantized insertion depth for the current insertion/retraction cycle is moved up to the next quantization level. In some examples, the deepest quantized insertion depth for the current insertion/retraction cycle is moved up to the next quantization level by decrementing the deepest quantized insertion depth for the current insertion/retraction cycle. Once the deepest quantized insertion depth for the current insertion/retraction cycle is moved up, the quantized insertion depth is again compared to the deepest quantized insertion depth for the current insertion/retraction cycle using process 1118 in case more than one bin depth should be aggregated, output, and cleared using processes 1120-1124.

As discussed above and further emphasized here, FIGS. 11A and 11B are merely examples which should not unduly limit the scope of the claims. One of ordinary skill in the art would recognize many variations, alternatives, and modifications. In some embodiments, the no movement case may be treated differently. In some examples, when the direction is determined to be no movement during process 1108, the current positional data may be alternatively processed using processes 1118-1126 rather than processes 1110-1114. In some examples, no movement may result from a pause in either insertion or retraction so that when no movement is determined during process 1108, the current positional data is processed by processes 1110-1114 as a temporary pause in insertion when the direction for the previous positional data was associated with an insertion and the current positional data is processed by processes 1116-1126 as a temporary pause in retraction when the direction for the previous positional data was associated with a retraction. In some examples, when multiple consecutive positional data points are determined to be no movement, the classification of the current positional data depends on whether the most recent directional determination (other than no movement) was insertion or retraction. In some examples, a limited number (e.g., 2, 3, 4, 5, or more) of consecutive positional data points associated with no movement may be collected and added to the respective insertion or retraction bin before further consecutive positional data points associated with no movement are discarded. In some examples, the limited number of consecutive positional data points associated with no movement may be collected for a predetermined period of time before further consecutive positional data points associated with no movement are discarded.

In some embodiments, the aggregation of process 1120 may be determined differently. In some examples, no distinction is made between insertion positional data and retraction positional data such that the insertion bins and the retraction bins are the same and processes 1110 and 1116 may be combined as a single process between processes 1106 and 1108. In some examples, a separate collection of bins for positional data associated with no movement is aggregated with the corresponding insertion bin and retraction bin during process 1120. In some examples, each of the insertion bins and/or each of the retraction bins may be replaced by a single aggregate at the quantized insertion depth. In some examples, the single aggregate may be determined using a running aggregation, such as exponential smoothing, where each current positional data that is added to the respective bin during process 1110 or 1116 is combined with the running aggregation. In some examples, a single running aggregation may be used for current positional data associated with both insertion and retraction so that the collections of insertion bins and retraction bins are replaced with a collection of running aggregations at each of the possible quantized insertion depths.

In some embodiments, current positional data may be collected from multiple locations along the medical device using a shape sensor, such as shape sensor 222, or using multiple EM sensors of tracking system 230. Each of the current positional data points may be associated with its own respective current insertion depth, which is separately quantized using a process similar to process 1106 and is then added to a corresponding insertion bin or retraction bin by processes similar to processes 1110 and 1116, respectively. In some examples, when the multiple locations are spaced apart by the bin size, the separate quantizations may be replaced by a single quantization for the current insertion depth of one of the locations (e.g., the most distal location) with the other quantized current insertions depths being determined based on the spacing from the selected one of the locations. Additionally, the determinations of processes 1112 and/or 1118 may be based on the quantized insertion depth of the most distal of the locations for which the current positional data is detected. In this way, positional data from more proximal locations along the medical device may contribute positional data for bins above the recorded deepest bin until the medical device is retracted above the recorded deepest bin.

FIGS. 12A-12D illustrate exemplary bin structures during various stages of processing sensor data according to method 1100. More specifically, each of FIGS. 12A-12D show insertion and retraction bins corresponding to exemplary quantized insertion depths i through i+4 holding positional data ($P_1$-$P_{20}$) collected using method 1100. FIG. 12A shows the insertion and retraction bins after a period of insertion followed by the beginning of a retraction. Positional data corresponding to the insertion are shown as positional data $P_1$-$P_{13}$ that are distributed across the insertion bins corresponding to quantized insertion depths i through i+4. As shown, $P_1$-$P_3$ have been added to the insertion bin at quantized insertion depth i, $P_4$ and $P_5$ have been added to the insertion bin at quantized insertion depth i+2, $P_6$-$P_{10}$ have been added to the insertion bin at quantized insertion depth i+3, and $P_{11}$-$P_{13}$ have been added to the insertion bin at quantized insertion depth i+4. The larger number of positional data in the insertion bin at quantized insertion depth i+3 may correspond to one or more periods of no movement and/or a slower insertion rate while the medical device was at quantized insertion depth i+3 relative to the other quantized insertion depths. The lack of position data in the insertion bin at quantized insertion depth i+1 may correspond to a rapid insertion across this quantized insertion depth such that no positional data was collected or received. As positional data $P_1$-$P_{13}$ was collected, the deepest quantized insertion depth for the current insertion/retraction cycle was updated until it reached quantized insertion depth i+4. After collecting positional data $P_{13}$, the direction of the medical device changed to retraction and positional data $P_{14}$-$P_{16}$ were collected and added to the retraction bin at quantized insertion depth i+4. Because the quantized insertion depth of positional data $P_{14}$-$P_{16}$ is not yet above the deepest quantized insertion depth for the current insertion/retraction cycle of i+4, processes 1120-1126 to aggregate, output, and clear the positional data at quantized insertion depth i+4 has not yet occurred.

FIG. 12B shows the insertion and retraction bins after a first positional data point ($P_{17}$) at a quantized insertion depth (i+3) above the current deepest bin (i+4) is received. After $P_{17}$ is saved in the retraction bin at quantized insertion depth i+3 during process 1116, process 1118 triggers the performance of processes 1120-1126 because the quantized insertion depth of $P_{17}$ is i+3, which is above the deepest bin of i+4. At process 1120, the positional data ($P_{11}$-$P_{13}$) in the insertion bin at quantized insertion depth i+4 is aggregated to become the first aggregation value, the positional data ($P_{14}$-$P_{16}$) in the retraction bin at quantized insertion depth i+4 is aggregated to become the second aggregation value, and the first and second aggregation values are aggregated to become the aggregate positional value. The aggregate position value is then output by process 1122, the insertion bin and the retraction bin at quantized insertion depth i+4 are cleared by process 1124, and the deepest quantized insertion depth for the current insertion/retraction cycle becomes i+3 by process 1126.

FIG. 12C shows the insertion and retraction bins after additional positional data points ($P_{18}$ and $P_{19}$) are collected and stored in the retraction bin at quantized insertion depth i+3. Because both $P_{18}$ and $P_{19}$ are at the same quantized insertion depth (i+3) as the deepest quantized insertion depth for the current insertion/retraction cycle (i+3), no further aggregation, outputting, and clearing has yet occurred. The deepest quantized insertion depth for the current insertion/retraction cycle remains at quantized insertion depth i+3.

FIG. 12D shows the insertion and retraction bins after a first positional data point ($P_{20}$) is collected at a quantized insertion depth (i+1) above the deepest quantized insertion depth for the current insertion/retraction cycle (i+3). FIG. 12D shows the scenario where, during a retraction, one or more quantized insertion depths are skipped without additional positional data being obtained. In some examples, this may occur due to a rapid retraction through these quantized insertion depths. Because quantized insertion depth i+2 was skipped, the loop of processes 1120-1126 is repeated twice to aggregate, output, and clear the positional data at quantized insertion depths i+3 and i+2, respectively, and to move the deepest quantized insertion depth for the current insertion/retraction cycle to quantized insertion depth i+1. FIG. 12D further shows the scenario where one of the bins, in this case the retraction bin at quantized insertion depth i+2, includes no positional data so that the retraction bin at quantized insertion depth i+2 is not included in the aggregation of process 1120 or the clearing of process 1124. Although not shown in the FIGS. 12A-12D, the same will eventually occur to the insertion bin at quantized insertion depth i+1, because the insertion bin at quantized insertion depth i+1 does not include any positional data.

FIG. 13A illustrates an exemplary graph 1310 of raw positional data from a medical device that traversed a patient passageway for comparison with FIG. 13B, which is an exemplary graph 1350 of the same positional data after the raw data is processed, such as in the manner discussed in the processes of FIGS. 10 and/or 11A. The raw and processed positional data are represented by the dots in FIGS. 13A and 13B. The dots are clustered in such close proximity and density that they seem to form a line.

The raw positional data in graph 1310 may be from a medical device that traversed a passageway in the manner indicated by arrows 1311-1320. As shown and indicated by arrow 1311 and the data points of graph 1310, the medical device was inserted into the passageway, which may have been guided by the operator, to one side of a first fork and then to one side of a second fork until the medical device reached the end of the second fork. The raw positional data is captured during the insertion and may be displayed in graph 1310. As indicated by arrow 1312 and the data points of graph 1310, the medical device is retracted back to the beginning of the second fork. As shown, even though the medical device traversed the same passageway on both insertion and retraction, the positional data is not an exact match. This is because, as discussed above, the medical device may experience kinks in the line as it moves, move the passageway as the device moves, move from one wall toward another wall of the passageway, include sensor noise, be the result of changes in anatomic phase, and/or the like. As such, the raw positional data indicates that the insertion path is different from the retraction path.

Continuing with the direction of the medical device, as indicated by arrow 1313, the medical device, after partially being retracted back to the second fork, may be inserted into the other side of the second fork. Then, as indicated by arrow 1314, the medical device is retracted back to the first fork. The medical device, as indicated by arrow 1315, is then inserted into the second side of the first fork into a first side of a third fork and continuing to the end of a first side of a fourth fork. The medical device, as indicated by arrow 1316, is then retracted to the fourth fork where it was inserted into the second side of the fourth fork, as indicated by arrow 1317. As indicated by arrow 1318, the medical device is then retracted back to the third fork and then inserted into the second side of the third fork, as indicated by arrow 1319. Finally, as indicated by arrow 1320, the medical device is retracted back to the insertion point.

As shown by the positional data collected and shown in graph 1310, the insertion paths do not generally match the retraction paths. As such, it is difficult to discern the shape of the anatomic passageway that is mapped. However, the raw data used for graph 1310 may be processed by the methods of FIGS. 10 and/or 11A, and the processed (i.e. output) data may represent the traversed passageway as shown in graph 1350 of FIG. 13B. As shown in graph 1350, the processed anatomic passageway is much easier to discern and likely more accurate to the actual passageway traversed.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a non-transitory computer-readable storage media, including any media that can store information including an optical medium, semiconductor medium, and magnetic medium. Computer-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method performed by a medical system comprising:
driving, via a drive unit, a flexible elongate device along a plurality of passageways;
determining, via a tracking system communicatively coupled to the drive unit, positional data of the flexible elongate device using one or more sensors coupled to the flexible elongate device;
providing, via an actuator system communicatively coupled to the drive unit, motion of the flexible elongate device along the plurality of passageways, the motion including insertion and retraction within the plurality of passageways;
recording, via one or more hardware processors communicatively coupled to the tracking system and the actuator system, the positional data, wherein the positional data includes a first plurality of positional data points recorded during a first insertion of the flexible elongate device into a first passageway of the plurality of passageways and a second plurality of positional data points recorded during a first retraction of the flexible elongate device within the first passageway;
associating, via the one or more hardware processors, the first plurality of positional data points with the second plurality of positional data points by labeling the first plurality of positional data points and the second plurality of positional data points as first common passageway positional data points; and
registering, via the one or more hardware processors, the positional data with a model of the plurality of passageways, wherein the registering includes matching the first common passageway positional data points with corresponding first common passageway model data points.

2. The method of claim 1, wherein the positional data further includes a third plurality of positional data points recorded during a second insertion of the flexible elongate device into a second passageway of the plurality of passageways and a fourth plurality of positional data points recorded during a second retraction of the flexible elongate device within the second passageway.

3. The method of claim 2, further comprising:
labeling the third plurality of positional data points and the fourth plurality of positional data points as second common passageway positional data points, wherein the registering further includes matching the second common passageway positional data points with corresponding second common passageway model data points.

4. The method of claim 2, wherein the second insertion of the flexible elongate device occurs after the first insertion of the flexible elongate device and after the first retraction of the flexible elongate device.

5. The method of claim 4, wherein the second retraction of the flexible elongate device occurs after the second insertion of the flexible elongate device.

6. A medical system comprising:
an elongated flexible device;
a tracking system that determines positional data of the elongated flexible device;
an actuator system that provides motion of the elongated flexible device within a plurality of anatomical passageways of a patient, the motion including insertion and retraction within the plurality of anatomical passageways; and
one or more hardware processors coupled to the tracking system and the actuator system, the one or more hardware processors being configured to:
record the positional data, wherein the positional data comprises a first plurality of positional data points recorded during a first insertion of the elongated flexible device into a first passageway and a second plurality of positional data points recorded during a first retraction of the elongated flexible device within the first passageway;
associate the first plurality of positional data points with the second plurality of positional data points by labeling the first plurality of positional data points and the second plurality of positional data points as first common passageway positional data points; and
register the positional data with a model of the plurality of anatomical passageways of the patient, wherein the registering includes matching the first common passageway positional data points with corresponding first common passageway model data points.

7. The medical system of claim 6, wherein the elongated flexible device comprises a catheter.

8. The medical system of claim 6, wherein the tracking system comprises at least one of a shape sensor, a position sensor, or an imaging system.

9. The medical system of claim 6, wherein the tracking system comprises a fiber optic shape sensor.

10. The medical system of claim 6, wherein the actuator system comprises at least one of an actuator, an encoder, a resolver, or a potentiometer.

11. The medical system of claim 10, wherein the actuator system is located at a proximal portion of the elongated flexible device.

12. The medical system of claim 6, wherein the one or more hardware processors are further configured to:
store a first set of positional data points of the first plurality of positional data points at an insertion distance during the first insertion of the elongated flexible device;
store a second set of positional data points of the second plurality of positional data points at the insertion distance during the first retraction of the elongated flexible device; and
combine the first and the second sets of positional data points to create a third set of positional data points.

13. The medical system of claim 12, wherein the first set of positional data points is stored in a first cell in a matrix, the second set of positional data points is stored in a second cell in the matrix, and the first and second cells in the matrix are cleared after the third set of positional data points is created.

14. The medical system of claim 12, wherein the one or more hardware processors are further configured to combine at least one positional data point at each insertion distance between a current insertion distance of the elongated flexible device and a deepest insertion distance for the elongated flexible device during a current insertion and retraction cycle to determine at least one aggregate positional data point for each insertion depth.

15. The medical system of claim 12, wherein the insertion distance comprises a quantized insertion distance.

16. The medical system of claim 12, wherein combining the first and the second sets of positional data points comprises averaging the first set and the second set of positional data points.

17. A non-transitory machine-readable medium comprising a plurality of machine-readable instructions which when executed by one or more processors associated with a device are adapted to cause the one or more processors to perform operations including:
driving, via a driving system, a flexible elongate device along a plurality of passageways;
recording, via one or more hardware processors, positional data using one or more sensors coupled to the flexible elongate device, wherein the positional data includes a first plurality of positional data points recorded during a first insertion of the flexible elongate device into a first passageway and a second plurality of positional data points recorded during a first retraction of the flexible elongate device within the first passageway;
associating, via the one or more hardware processors, the first plurality of positional data points with the second plurality of positional data points by labeling the first plurality of positional data points and the second plurality of positional data points as first common passageway positional data points; and
registering, via the one or more hardware processors, the positional data with a model of the plurality of passageways, wherein the registering includes matching the first common passageway positional data points with corresponding first common passageway model data points.

* * * * *

UNITED STATES PATENT AND TRADEMARK OFFICE
CERTIFICATE OF CORRECTION

| | | |
|---|---|---|
| PATENT NO. | : 11,882,990 B2 | |
| APPLICATION NO. | : 16/481954 | |
| DATED | : January 30, 2024 | |
| INVENTOR(S) | : Tao Zhao and Timothy D. Soper | |

It is certified that error appears in the above-identified patent and that said Letters Patent is hereby corrected as shown below:

On the Title Page

Under "( * ) Notice:", delete the following:
"This patent is subject to a terminal disclaimer."

Signed and Sealed this
Sixteenth Day of April, 2024

Katherine Kelly Vidal
Director of the United States Patent and Trademark Office